(12) United States Patent
Park et al.

(10) Patent No.: US 12,287,345 B2
(45) Date of Patent: Apr. 29, 2025

(54) APPARATUS AND METHOD FOR MEASURING GLYCATED HEMOGLOBIN

(71) Applicant: Boditech Med Inc., Chuncheon-si (KR)

(72) Inventors: Kyung Won Park, Seongnam-si (KR); Chang Sang Moon, Hwaseong-si (KR); Yun Suk Choi, Suwon-si (KR); Bo Ram Jeon, Hwaseong-si (KR)

(73) Assignee: Boditech Med Inc., Chuncheon-si (KR)

( * ) Notice: Subject to any disclaimer, the term of this patent is extended or adjusted under 35 U.S.C. 154(b) by 908 days.

(21) Appl. No.: 17/087,169

(22) Filed: Nov. 2, 2020

(65) Prior Publication Data

US 2021/0325410 A1    Oct. 21, 2021

Related U.S. Application Data

(63) Continuation of application No. PCT/KR2020/008881, filed on Jul. 8, 2020.

(30) Foreign Application Priority Data

Apr. 20, 2020    (KR) ................ 10-2020-0047679

(51) Int. Cl.
     *G01N 33/72*      (2006.01)
     *B01L 3/00*      (2006.01)
     (Continued)

(52) U.S. Cl.
     CPC .......... *G01N 33/723* (2013.01); *B01L 3/5023* (2013.01); *G01N 35/00732* (2013.01);
     (Continued)

(58) Field of Classification Search
     CPC .......... G01N 33/723; G01N 35/00732; G01N 35/1002; G01N 35/1004; B01L 3/5023; B01L 3/5029
     See application file for complete search history.

(56) References Cited

U.S. PATENT DOCUMENTS

| 4,251,159 | A | 2/1981 | White |
| 5,149,501 | A | 9/1992 | Babson et al. |
| | | (Continued) | |

FOREIGN PATENT DOCUMENTS

| CN | 107255728 A | 10/2017 |
| CN | 107356587 A | 11/2017 |
| | (Continued) | |

OTHER PUBLICATIONS

Office Action issued in KR 10-2020-0047679; mailed by the Korean Intellectual Property Office on Jun. 24, 2020.

(Continued)

*Primary Examiner* — Brian R Gordon
*Assistant Examiner* — Dwan A Gerido
(74) *Attorney, Agent, or Firm* — Studebaker Brackett PLLC

(57) ABSTRACT

Provided is a glycated hemoglobin measuring apparatus. The apparatus for measuring glycated hemoglobin includes a cartridge for receiving blood and a plurality of chemicals, a rotating tray for rotating the cartridge, wherein the cartridge is disposed inside the rotating tray, a driver having a nozzle disposed above the cartridge and movable in a vertical direction, and a measurement unit located above the cartridge and measuring glycated hemoglobin of the blood, wherein the driver sucks at least one of the blood, the plurality of chemicals, and mixed solution of the blood and the plurality of chemicals into the nozzle or discharges the sucked at least one into the cartridge such that the blood is chemically treated through the plurality of chemicals.

6 Claims, 24 Drawing Sheets

(51) Int. Cl.
  *G01N 35/00* (2006.01)
  *G01N 35/10* (2006.01)
(52) U.S. Cl.
  CPC ..... *G01N 35/1002* (2013.01); *G01N 35/1004* (2013.01); *B01L 2200/04* (2013.01); *B01L 2200/0689* (2013.01); *B01L 2200/10* (2013.01); *B01L 2200/14* (2013.01); *B01L 2200/16* (2013.01)

(56) References Cited

U.S. PATENT DOCUMENTS

| | | | |
|---|---|---|---|
| 10,371,709 | B2 | 8/2019 | Kim et al. |
| 2010/0267048 | A1 | 10/2010 | Tanaka et al. |
| 2014/0017814 | A1 | 1/2014 | Tanaka et al. |
| 2016/0291009 | A1 | 10/2016 | Kim et al. |
| 2017/0292967 | A1 | 10/2017 | Kim et al. |
| 2018/0021783 | A1* | 1/2018 | Arlett ............... G01N 35/00029 435/287.2 |
| 2018/0136194 | A1 | 5/2018 | Sinn Blandy et al. |

FOREIGN PATENT DOCUMENTS

| | | | |
|---|---|---|---|
| CN | 207366448 U | | 5/2018 |
| CN | 110118878 A | | 8/2019 |
| CN | 110672861 A | | 1/2020 |
| JP | 11-304797 A | | 11/1999 |
| JP | 2003-329696 A | | 11/2003 |
| JP | 2006-125868 A | | 5/2006 |
| JP | 2016-024055 A | | 2/2016 |
| JP | 2016-536590 A | | 11/2016 |
| JP | 2017-116544 A | | 6/2017 |
| JP | 2017-187496 A | | 10/2017 |
| JP | 2019-196917 A | | 11/2019 |
| KR | 10-2012-0114750 A | | 10/2012 |
| KR | 10-2014-0071062 A | | 6/2014 |
| KR | 10-2016-0051253 A | | 5/2016 |
| KR | 10-2017-0115692 A | | 10/2017 |
| KR | 10-1885964 B1 | | 8/2018 |
| KR | 20170115692 | * | 10/2018 |
| WO | 2008/044594 A1 | | 4/2008 |

OTHER PUBLICATIONS

International Search Report issued in PCT/KR2020/008881; mailed Jan. 15, 2021.
An Office Action mailed by the Korean Intellectual Property Office on Apr. 29, 2021, which corresponds to Korean Patent Application No. 10-2021-0020330 and is related to U.S. Appl. No. 17/087,169.
An Office Action mailed by China National Intellectual Property Administration on Dec. 13, 2023, which corresponds to Chinese Patent Application No. 202080002024.4 and is related to U.S. Appl. No. 17/087,169.
An Office Action; "Notice of Reasons for Refusal," mailed by the Japanese Patent Office on Aug. 2, 2022, which corresponds to Japanese Patent Application No. 2020-564203 and is related to U.S. Appl. No. 17/087,169.
An Office Action; "Notice of Reasons for Refusal," mailed by the Japanese Patent Office on Mar. 28, 2023, which corresponds to Japanese Patent Application No. 2020-564203 and is related to U.S. Appl. No. 17/087,169.
The extended European search report issued by the European Patent Office on Jan. 26, 2024, which corresponds to European Patent Application No. 20931920.1-1101 and is related to U.S. Appl. No. 17/087,169.

* cited by examiner

APPARATUS AND METHOD FOR MEASURING GLYCATED HEMOGLOBIN

CROSS-REFERENCE TO RELATED APPLICATIONS

The present application is a continuation of International Patent Application No. PCT/KR2020/008881, filed on Jul. 8, 2020, which is based upon and claims the benefit of priority to Korean Patent Application No. 10-2020-0047679 filed on Apr. 20, 2020. The disclosures of the above-listed applications are hereby incorporated by reference herein in their entirety.

BACKGROUND

Embodiments of the inventive concept described herein relate to an apparatus and a method for measuring glycated hemoglobin, and more particularly, relate to an apparatus and a method for automatically performing a chemical treatment on blood and measuring glycated hemoglobin using a cartridge equipped with both the blood and chemical, a rotation scheme, and a nozzle.

Diabetes is a group of metabolic diseases in which blood glucose is maintained above a normal range for a long time. When the blood glucose is maintained high, acute complications such as a diabetic ketoacidosis, a hyperosmolar hyperglycemic nonketotic coma, and the like, and long-term complications such as a cardiovascular disease, a stroke, a hyperosmolar hyperglycemic nonketotic coma, a diabetic ulcer, a diabetic retinopathy, and the like may occur. Therefore, diabetic patients need constant management to prevent various complications by regularly testing the blood glucose and to maintain a blood glucose level at an appropriate level. Therefore, the blood glucose is an important indicator for diagnosing or managing the diabetes.

The blood glucose refers to a concentration of glucose contained in blood, and a level thereof is not fixed and changes from time to time affected by factors such as a diet, a physical activity, and the like. Therefore, it is important to determine average blood glucose, not instantaneous blood glucose. The most widely used method to determine long-term blood glucose is a method for measuring a glycated hemoglobin (HbA1c) level.

The glycated hemoglobin (HbA1c) refers to a form in which glucose in a blood vessel, that is, the blood glucose, is bound to hemoglobin normally present in a red blood cell. When the blood glucose increases, the blood glucose that binds to the hemoglobin increases, resulting in an increase in the glycated hemoglobin. In addition, because the bound glucose is not used and stays bound to the hemoglobin, an average level of the glycated hemoglobin is maintained. In one example, because an average lifespan of the red blood cell is about 3 months, the glycated hemoglobin reflects an average blood glucose level for about 3 months.

SUMMARY

Embodiments of the inventive concept provide an apparatus and a method that allow a plurality of operations to be taken for measuring glycated hemoglobin to be performed automatically instead of manually.

In addition, embodiments of the inventive concept provide an apparatus and a method using an information pattern (e.g., a barcode and a QR code) that may minimize an error occurring in a glycated hemoglobin measurement process.

The purposes to be achieved by the inventive concept are not limited to the purposes mentioned above. Other purposes not mentioned will be clearly understood by those skilled in the art from following descriptions.

According to an exemplary embodiment, an apparatus for measuring glycated hemoglobin includes a cartridge for receiving blood and a plurality of chemicals, a rotating tray for rotating the cartridge, wherein the cartridge is disposed inside the rotating tray, a driver having a nozzle disposed above the cartridge and movable in a vertical direction, and a measurement unit located above the cartridge and measuring glycated hemoglobin of the blood. The driver that allows the blood to be chemically treated through the plurality of chemicals may suck at least one of the blood, the plurality of chemicals, and mixed solution of the blood and the plurality of chemicals into the nozzle or discharge the sucked at least one into the cartridge.

Other specific details of the inventive concept are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
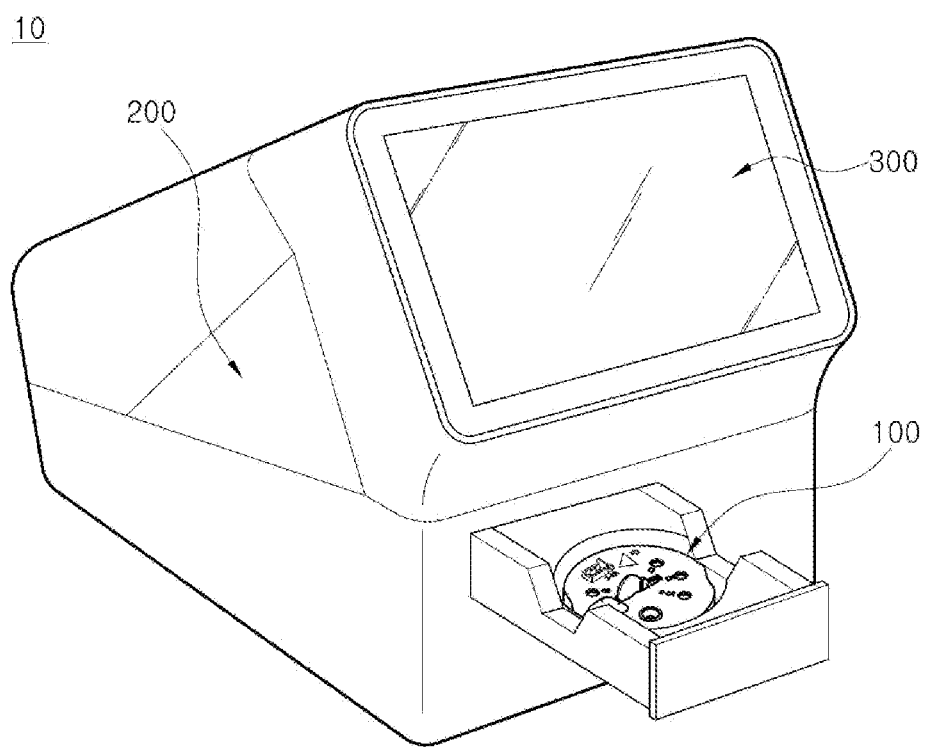
FIG. 1 is a perspective view schematically illustrating a glycated hemoglobin measuring apparatus according to an embodiment of the inventive concept.

Advantages and features of the inventive concept, and a method of achieving them will become apparent with reference to embodiments described below in detail together with the accompanying drawings. However, the inventive concept is not limited to the embodiments disclosed below, but may be implemented in various different forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "under", "above", "upper", and the like, may be used herein for ease of explanation to describe a correlation between one component and other components as illustrated in the figures. It will be understood that the spatially relative terms are intended to encompass different orientations of the device in use or in operation, in addition to the orientation depicted in the figures. For example, when the device in the drawing is turned over, elements described as "below" or "beneath" or "under" other elements or features would then be oriented "above" the other elements or features. Thus, the example terms "below" and "under" may encompass both an orientation of above and below. The device may be otherwise oriented for example, rotated 90 degrees or at other orientations, and the spatially relative descriptors used herein should be interpreted accordingly.

Hereinafter, embodiments of the inventive concept will be described in detail with reference to the accompanying drawings.

In the present specification, "solid reagent" is reagent used to measure glycated hemoglobin, which refers to reagent that serves to induce hemolysis. That is, hemolysis reagent plays a role in disrupting a red blood cell in blood to induce hemoglobin to flow out of a blood cell.

In the present specification, "decomposition solution" refers to reagent that serves to clean an object to be tested.

Figure 2:
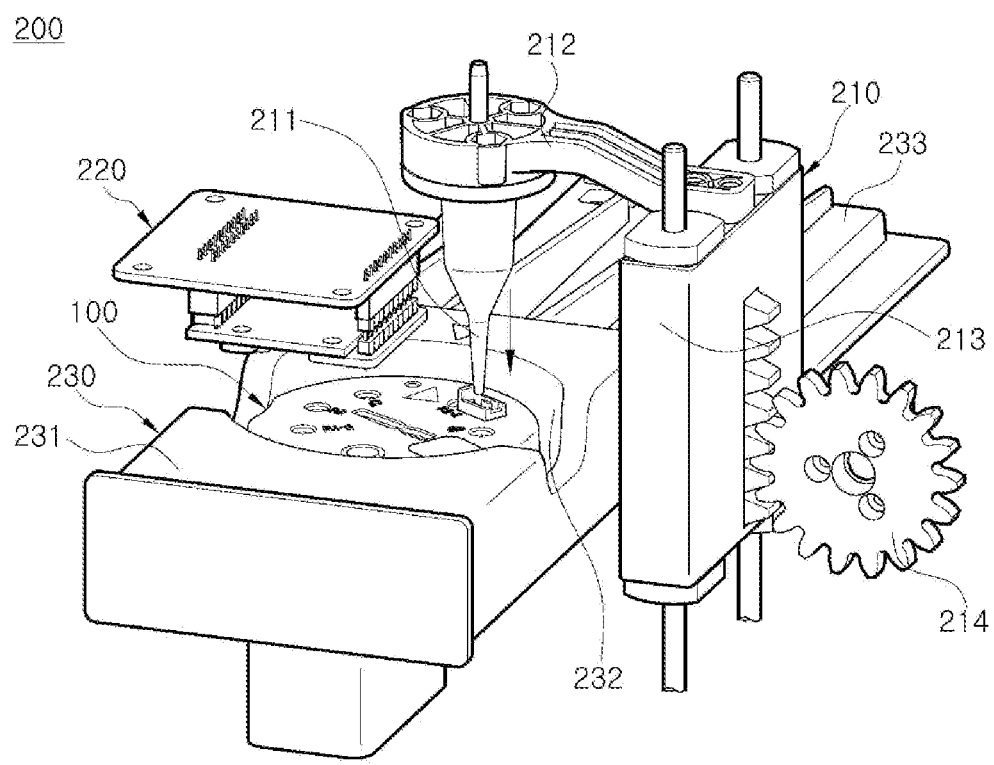
FIG. 2 is a perspective view schematically illustrating an internal configuration of a glycated hemoglobin measuring apparatus according to an embodiment of the inventive concept.
Figure 3A:
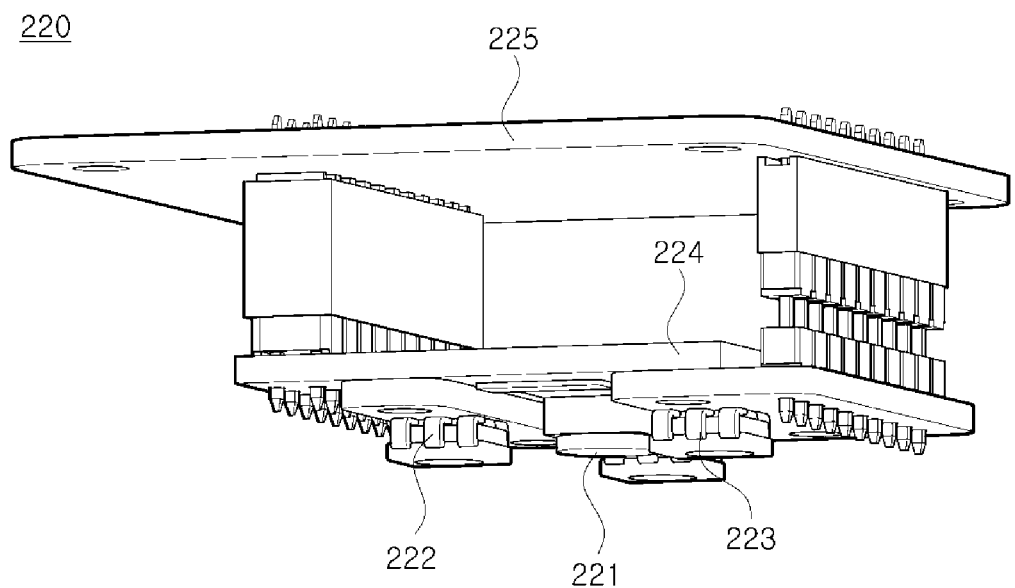
FIGS. 3A and 3B are respectively a perspective view and a conceptual diagram illustrating a measurement unit according to an embodiment of the inventive concept.
Figure 3B:
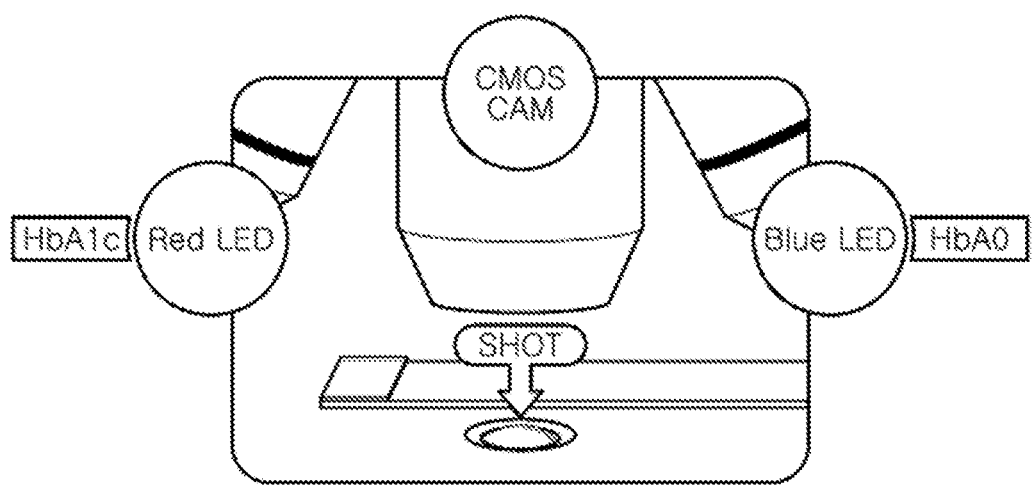

FIG. 1 is a perspective view schematically illustrating a glycated hemoglobin measuring apparatus according to an embodiment of the inventive concept. FIG. 2 is a perspective view schematically illustrating an internal configuration of a glycated hemoglobin measuring apparatus according to an embodiment of the inventive concept. FIGS. 3A and 3B are respectively a perspective view and a conceptual diagram illustrating a measurement unit according to an embodiment of the inventive concept.

In an embodiment, a glycated hemoglobin measuring apparatus 10 of the inventive concept may include a light source and a measurement unit (an imaging apparatus) therein, may capture an information pattern (a barcode or a QR code) in a cartridge 100 to set an error correction condition that may occur every time the cartridge 100 is produced, and may perform rotation, ascending, and descending by a motor when the cartridge 100 is inserted. For example, the cartridge 100 may be a kit that puts a blood sample therein and performs a chemical treatment to measure the glycated hemoglobin, and the glycated hemoglobin measuring apparatus 10 may acquire a captured image while providing light to the chemically treated blood. For example, a CMOS camera may capture the image based on the rotation of the cartridge 100 at a fixed position inside the apparatus 10. All operations may be performed automatically without a need for manipulation of a user when the user simply puts the blood-inserted cartridge 100 in the apparatus 10.

Specifically, referring to FIGS. 1 to 3A and 3B, in an embodiment, the glycated hemoglobin measuring apparatus 10 may include the cartridge 100, a measuring apparatus body 200, and a monitor 300. The cartridge 100 may receive therein blood, which corresponds to an object to be measured, and a plurality of chemicals for performing the chemical treatment on the blood for measuring the glycated hemoglobin. The measuring apparatus body 200 may automatically perform the chemical treatment on the blood contained in the cartridge 100 and measure the glycated hemoglobin.

In an embodiment, the monitor 300 may visually display a progress and a result of the glycated hemoglobin measurement through a user interface specified in advance.

In an embodiment, the cartridge 100 may contain the blood and the plurality of chemicals therein. For example, the plurality of chemicals may include the solid reagent, the decomposition solution, and reaction solution. The cartridge 100 may include a blood receiving portion R1-1 in which the blood is received, a solid reagent receiving portion R1-2 in which the solid reagent is received, a decomposition solution receiving portion R2 in which the decomposition solution is received, a reaction solution receiving portion CL in which the reaction solution is received, a membrane receiving portion in which a membrane is received, a washing portion SP, and information pattern recognition portion B. That is, each of the components included in the cartridge 100 may mean a space capable of receiving a liquid or solid material therein.

In an embodiment, the measuring apparatus body 200 may include a driver 210, a measurement unit 220, and a rotating tray 230. FIG. 2 schematically shows an interior of the measuring apparatus body 200, so that an outer housing is not shown. However, the driver 210, the measurement unit 220, and the rotating tray 230 are arranged in the measuring apparatus body 200. In addition, the driver 210 may be positioned at an edge of the rotating tray 230 and extending to a vertical level higher than a vertical level of the rotating tray 230, and the measurement unit 220 may be positioned at the edge of the rotating tray 230 and above the rotating tray 230.

In an embodiment, the driver 210 may be equipped with a nozzle 211 that is located above the cartridge 100 and is movable in a vertical direction. For example, the driver 210 may suck at least one of the blood, the plurality of chemicals, and mixed solution thereof into the nozzle 211 by a preset volume, or discharge at least one of those sucked into the cartridge 100 such that the blood is subjected to the chemical treatment by the plurality of chemicals. That is, the driver 210 may transport the blood, the plurality of chemicals, or the mixed solution thereof contained in the cartridge 100 from one of a plurality of spaces defined inside the cartridge 100 to another space. Detailed operations related thereto will be described later in FIGS. 12 to 37.

In an embodiment, the driver 210 may include a motor (not shown) that provides a driving force such that the nozzle 211 may move in the vertical direction, a toothed portion 214 connected to the motor, a guide 213 that is engaged with the toothed portion 214 and is capable of the vertical movement based on a rotation of the toothed portion 214, and a connection portion 212 having one end connected to the guide 213 and the other end connected to the nozzle 211 and located above the cartridge 100. Each of the components of the driver 210 may be constructed using known techniques (e.g., a piston pump).

For example, the driver 210 may have a fixed position, and accordingly, the nozzle 211 may be capable of only the vertical movement in a fixed position. In this connection, the fixed position may be a position where various holes defined in the cartridge 100 to be described later are placed by the rotation. That is, the blood or the plurality of chemicals of the cartridge 100 may be located at the fixed position of the nozzle 211 by the rotation of the rotating tray 230.

In an embodiment, the cartridge 100 may be disposed in the rotating tray 230, and the rotating tray 230 may rotate the cartridge 100. For example, the rotating tray 230 may perform a rotational motion of rotating by a required angle in each operation of the glycated hemoglobin measurement process to stop a corresponding component of the cartridge 100 at a set position (e.g., in a measurement region or below the nozzle 211). In addition, the rotating tray 230 is designed to maintain parallel and not to be deformed during the rotational motion. In one example, a rotating shaft of the rotating tray 230 may be rotated by an internal motor or the motor used together with the driver 210.

For example, the rotating tray 230 may rotate the cartridge 100 based on a preset angle such that the blood receiving portion R1-1, the solid reagent receiving portion R1-2, the decomposition solution receiving portion R2, the reaction solution receiving portion CL, and the membrane receiving portion are located in a region where the nozzle 211 moves vertically (or the position at which the nozzle 211 is fixed). That is, the cartridge 100 may be constructed to surround the internal spaces R1-1, R1-2, R2, and CL for receiving the blood or the plurality of chemicals therein in a circumferential direction around a center thereof. Further, the internal spaces of the cartridge 100 may be located below the nozzle 211 by the rotation of the rotating tray 230.

For example, the rotating tray 230 may include a rotating tray body 231 having a receiving groove 232 defined therein in which the cartridge 100 may be mounted and fixed, and a guide 233. The rotating tray body 231 may have a circular tray shape. In this connection, although not specifically illustrated in the drawing, a bottom portion of the rotating tray body 231 on which the cartridge 100 is mounted may be rotatably formed. In this connection, a rotational force may be provided by a separate motor or by the motor of the driver 210. In addition, the rotating tray body 231 may move along the guide 233 in a longitudinal direction of the guide 233. That is, as shown in FIG. 1, the rotating tray body 231 may be exposed to the outside by moving outward such that the cartridge 100 is able to be inserted therein, and may place the cartridge 100 below the nozzle 211 and the measurement unit 220 by moving inward. Known techniques may be applied for each component of the rotating tray 230.

In an embodiment, the measurement unit 220 may be located above the cartridge 100 and measure the glycated hemoglobin of the blood. The measurement unit 220 is an apparatus that measures the glycated hemoglobin contained in the blood in an optical method. Because the hemoglobin (Hb)), which is not bound to blood glucose, and the glycated hemoglobin (HbA1c) react in different wavelength bands, the measurement unit 220 measures an absorbance of a material to be measured to measure the glycated hemoglobin. The glycated hemoglobin measured in the measurement unit 220 is expressed as a numerical value. In an embodiment, the numerical value of the glycated hemoglobin may be expressed in units of HbA1c %. In this connection, the numerical value of the glycated hemoglobin is a ratio (%) of a concentration of the glycated hemoglobin (HbA1c) and a concentration of the hemoglobin (Hb). Calculation of the HbA1c % is based on a national glycohemoglobin standardization program (NGSP), an international federation of clinical chemistry and laboratory medicine (IFCC), a Japanese diabetes society (JDS), and the like.

For example, the measurement unit 220 may include a camera 221 for measuring the glycated hemoglobin from the chemically treated blood, a red LED 222 for emitting red light to the chemically treated blood, a blue LED 223 for emitting blue light to the chemically treated blood, a circuit board 224 on which the camera 221, the red LED 222, and the blue LED 223 are mounted, and a connection frame 225 for fixing the measurement unit 220 to be positioned in the measurement region. The camera 221 may be a CMOS CAM. Known technologies may be applied to each of the components of the measurement unit 220.

In one example, in an embodiment, the glycated hemoglobin measuring apparatus 10 may further include a sensor (not shown) or a printer (not shown). The sensor serves to sense the movements of the driver 210 and the rotating tray 230. Therefore, the driver 210 and the rotating tray 230 may rotate by set angles, and may accurately stop at positions specified in advance. The printer plays a role of printing out the glycated hemoglobin measurement result on paper.

Figure 4:
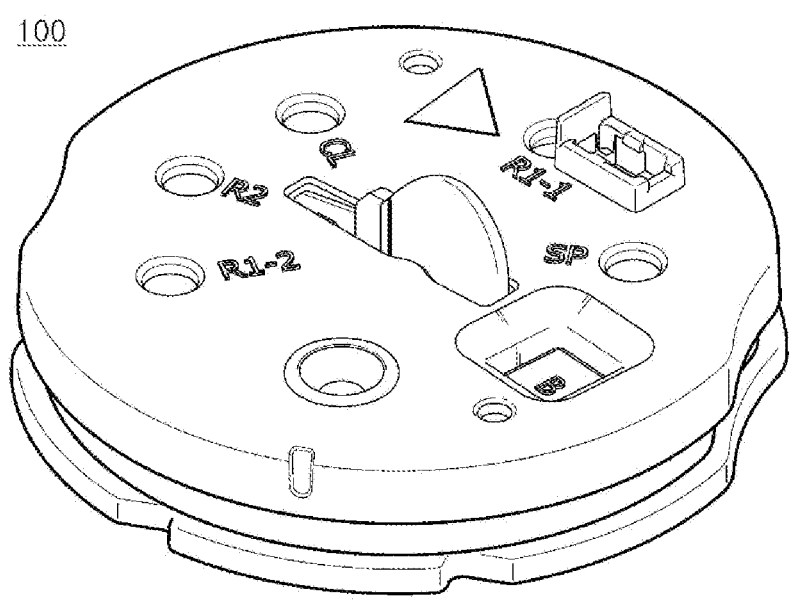
FIG. 4 is a perspective view schematically illustrating a cartridge according to an embodiment of the inventive concept.
Figure 5:
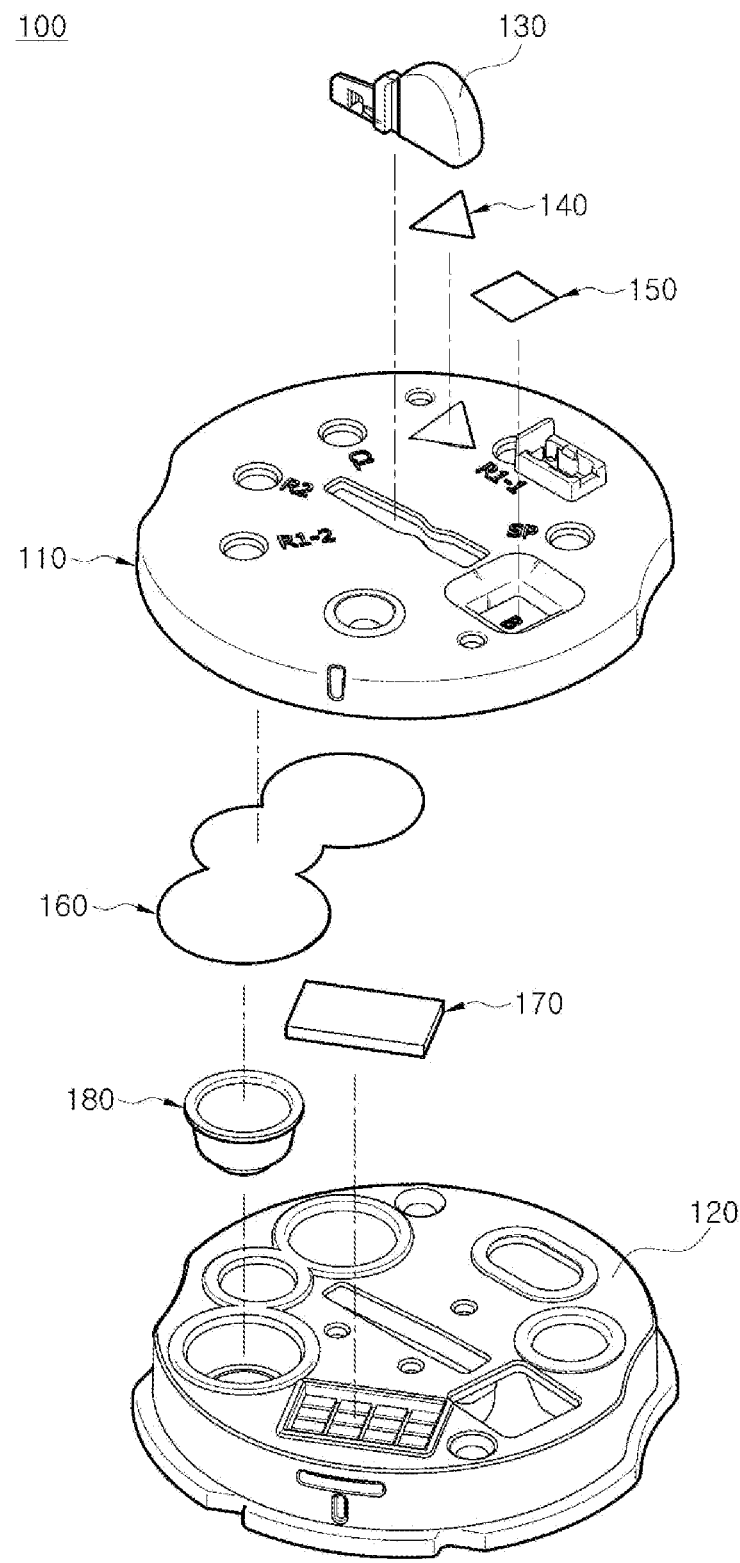
FIG. 5 is a schematic divided perspective view of a cartridge according to an embodiment of the inventive concept.
Figure 6:
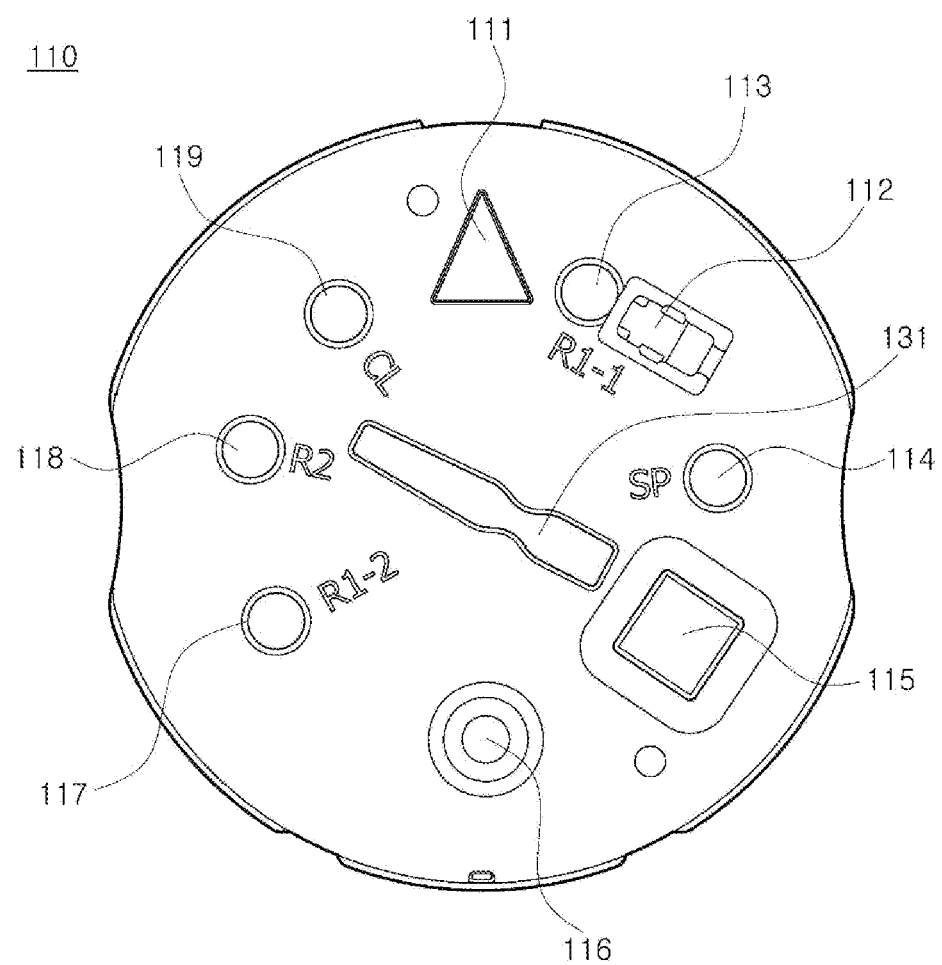
FIG. 6 is a diagram schematically illustrating an upper cartridge according to an embodiment of the inventive concept.
Figure 7:
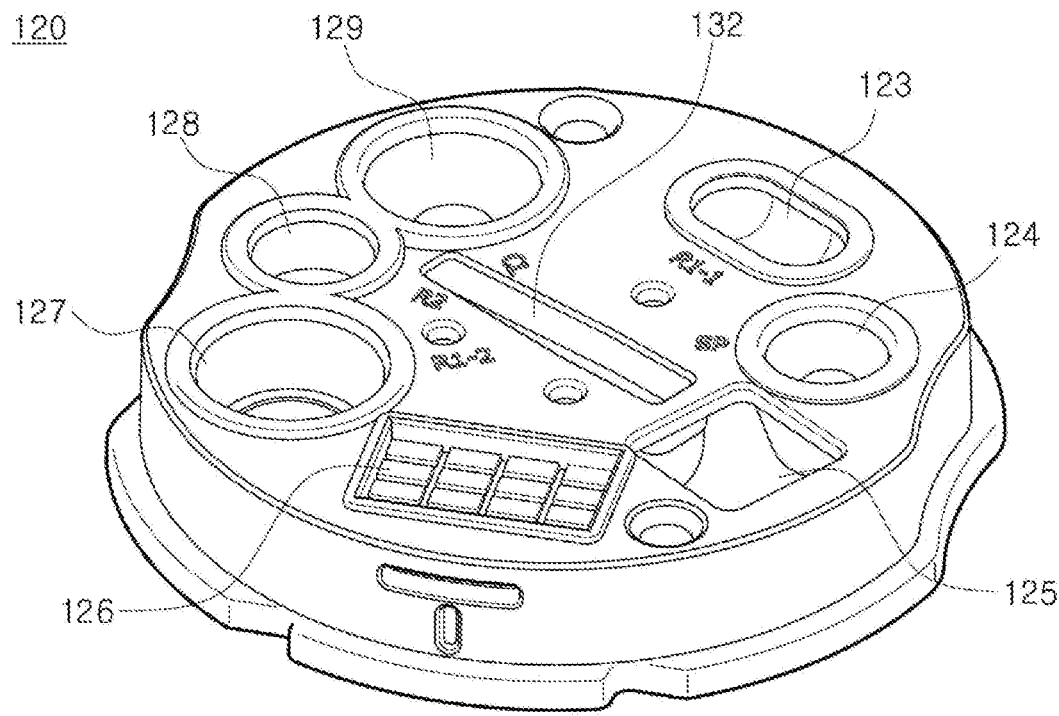
FIG. 7 is a diagram schematically illustrating a lower cartridge according to an embodiment of the inventive concept.
Figure 8:
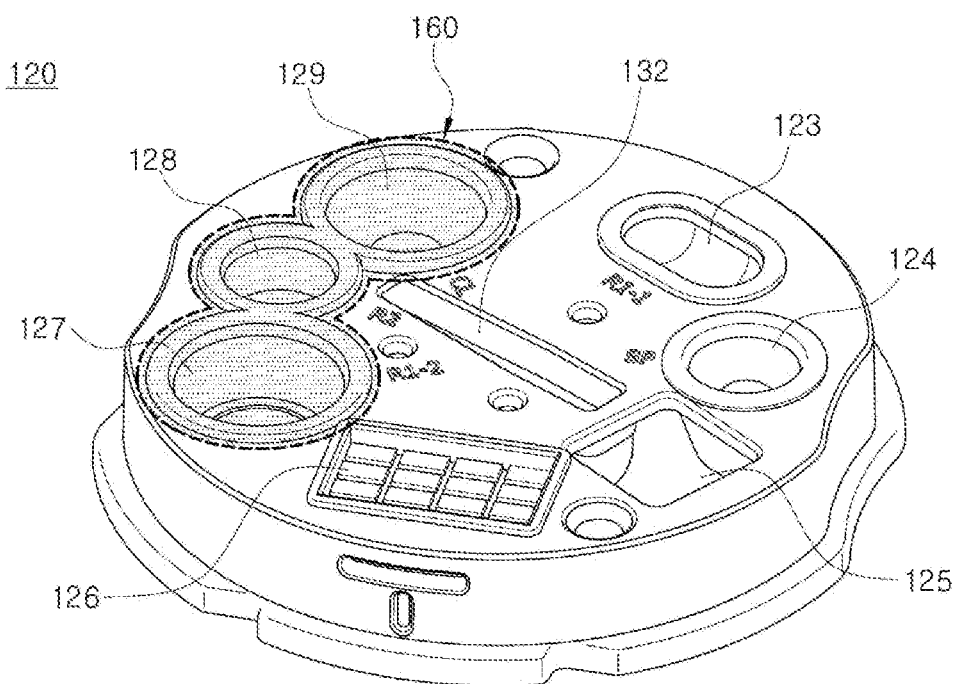
FIG. 8 is a diagram schematically illustrating a lower cartridge to which a sealing member according to an embodiment of the inventive concept is applied.

FIG. 4 is a perspective view schematically illustrating a cartridge according to an embodiment of the inventive concept. FIG. 5 is a schematic divided perspective view of a cartridge according to an embodiment of the inventive concept. FIG. 6 is a diagram schematically illustrating an upper cartridge according to an embodiment of the inventive concept. FIG. 7 is a diagram schematically illustrating a lower cartridge according to an embodiment of the inventive concept. FIG. 8 is a diagram schematically illustrating a lower cartridge to which a sealing member according to an embodiment of the inventive concept is applied. Further, FIGS. 9, 10A, 10B, and 11 are views illustrating a cartridge and a capillary.

Referring to FIGS. 4 to 11, the cartridge 100 may receive the blood and the plurality of chemicals therein. For example, the plurality of chemicals may include the solid reagent, the decomposition solution, and the reaction solution. For example, the cartridge 100 may be a circular kit.

In an embodiment, the cartridge 100 may have the plurality of spaces defined therein. The blood, the plurality of chemicals, a cleaning material, and the like may be contained in the plurality of spaces, respectively. The cartridge 100 may have a plurality of holes defined therein that may expose the plurality of spaces to the outside and may be penetrated by the nozzle 211 such that the nozzle 211 of the driver 210 may suck or discharge the blood and the like contained in the plurality of spaces. In this connection, the plurality of spaces will be described below named as the blood receiving portion R1-1, the washing portion SP, the solid reagent receiving portion R1-2, the decomposition solution receiving portion R2, the reaction solution receiving portion CL, and the membrane receiving portion. In one example, the information pattern recognition portion B may be a groove defined in a top surface of the cartridge 100.

For example, the blood receiving portion R1-1, the washing portion SP, the solid reagent receiving portion R1-2, the decomposition solution receiving portion R2, the reaction solution receiving portion CL, and the membrane receiving portion may be defined along the circumferential direction around the center of the circular cartridge 100.

For example, the blood receiving portion R1-1 may receive the blood therein, the solid reagent receiving portion R1-2 may receive the solid reagent therein, the decomposition solution receiving portion R2 may receive the decomposition solution therein, the reaction solution receiving portion CL may receive the reaction solution therein, and the membrane receiving portion may receive the membrane therein, the washing portion SP may contain a material for washing the nozzle 211 (hereinafter, the washing material), and the information pattern recognition portion B may receive an information pattern sticker 150 therein. A capacity that may be repeatedly supplied several times or more may be stored in advance for each of all of the solid reagent, the decomposition solution, the reaction solution, and the washing material. For example, before the cartridge 100 is actually manufactured and distributed, the plurality of chemicals may be stored therein in advance.

For example, the reaction solution may be diluent for adjusting a concentration of the blood. The decomposition solution is a kind of washer solution, and is reagent that provides the washing solution for washing the material to be measured to make the material to be measured to be easily measured. The decomposition solution may have effects other than the washing as necessary, and the effects thereof may not be limited to only the washing effect. The solid reagent is reagent used for measuring the glycated hemoglobin, and is reagent that plays a role in inducing hemolysis. That is, the solid reagent plays a role in inducing the hemoglobin to flow out of the blood cell by collapsing the red blood cell in the blood to measure the glycated hemoglobin in the collected blood. The solid reagent may have effects other than the hemolysis induction as necessary, and the effects thereof may not be limited to only the hemolytic effect.

In an embodiment, the cartridge 100 may include an upper cartridge 110, a lower cartridge 120, a capillary 130, a point sticker 140, the information pattern sticker 150, a sealing member 160, a membrane 170, and a container 180.

In an embodiment, the upper cartridge 110 may be coupled to the lower cartridge 120 to define an appearance of the cartridge 100 and protect the internal components. For example, the upper cartridge 110 may include a blood receiving hole 113 that exposes the blood to the outside such that the nozzle 211 may pass therethrough, a solid reagent receiving hole 117 that exposes the solid reagent to the outside, a decomposition solution receiving hole 118 that exposes the decomposition solution to the outside, a reaction solution receiving hole 119 that exposes the reaction solution to the outside, a membrane receiving hole 116 that exposes the membrane 170 to the outside, and a washing portion hole 114 that exposes the washing material to the outside.

In an embodiment, the upper cartridge 110 may further include a point sticker portion 111 in which the point sticker 140 is placed, a capillary insertion hole 112 into which the capillary 130 is inserted, a capillary groove 131 in which the capillary 130 is mounted, and an information pattern sticker portion 115 in which the information pattern sticker 150 is placed. In this connection, the point sticker portion 111, the capillary groove 131, and the information pattern sticker part 115 may be grooves.

In an embodiment, the lower cartridge 120 may include a blood receiving receptacle 123 for receiving the blood therein, a solid reagent receiving receptacle 127 for receiving the solid reagent therein, a decomposition solution receiving receptacle 128 for receiving the decomposition solution therein, a reaction solution receiving receptacle 129 for receiving the reaction solution therein, a membrane receiving receptacle 126 for receiving the membrane 170 therein, a washing portion receptacle 124 for receiving the washing material therein, a barcode region 125, and a capillary region 132.

In an embodiment, the point sticker 140 may indicate a direction in which the cartridge 100 is inserted into the rotating tray 230, and may be disposed in the point sticker portion 111.

In an embodiment, the information pattern sticker 150 may include information related to the plurality of chemicals, and may be disposed in the information pattern recognition portion B.

In an embodiment, the sealing member 160 may cover the solid reagent receiving receptacle 127, the decomposition solution receiving receptacle 128, and the reaction solution receiving receptacle 129 to prevent leakage of the solid reagent, the decomposition solution, and the reaction solution. For example, the sealing member 160 may be pierced when the nozzle 211 descends to suck the solid reagent, the decomposition solution, or the reaction solution. That is, the sealing member 160 has a sealing function for the distribution of the cartridge 100. That is, the sealing member 160 may actually be a component that is pierced by the nozzle 211 to open the closed space during the measurement.

In an embodiment, the membrane 170 is a component in which the material to be measured is substantially located as the mixed solution of the blood and the plurality of chemicals is contained therein. For example, the membrane 170 is made of a material having selective permeability. As a specific example, the membrane 170 may be a filter material capable of separating dissolved substances dissolved in liquid solution as well as performing general filtration of separating particles by selectively passing a specific constituent.

In another embodiment, the membrane 170 is a component that is replaced each time the glycated hemoglobin measurement is performed. As a specific example, because the cartridge 100 is in a form in which an upper portion and a lower portion thereof may be separated from each other, the membrane 170 may be replaced by separating the upper cartridge 110. Accordingly, the membrane 170 may be conveniently mounted or removed, and may be placed at an accurate position. In one example, the membrane 170 is maintained in a flat state without being curved such that the solution may be evenly distributed.

In an embodiment, the container 180 may be inserted into the solid reagent receiving receptacle 127 to receive the solid reagent therein.

In an embodiment, the capillary 130 is shipped together with the cartridge 100 in a state of being put into the cartridge 100 when the cartridge 100 is first manufactured and then is shipped. Thereafter, the user may use the capillary 130 by pulling out the capillary 130. The capillary 130 may store the blood filled by the user and may be seated in the capillary groove 131 defined in the upper cartridge 110. The capillary 130 may include a capillary insert 133 and a capillary receptacle 134 may be included. For example, the capillary insert 133 may be inserted into the capillary insertion hole 112 defined in the upper cartridge 110 and in communication with the blood receiving receptacle 123. Further, the capillary receptacle 134 may be connected to the capillary insert so as to be detachable by an external force and may receive pre-stored blood therein.

For example, the cartridge 100 may be distributed in a state containing the plurality of chemicals therein and including the capillary 130 not containing the blood therein. Thereafter, when actually measuring the glycated hemoglobin, the capillary 130 may be coupled with the cartridge 100 again as to be described below after collecting the blood, which is the material to be measured, in a state of being separated from the cartridge 100.

For example, the capillary receptacle 134 may be manufactured such that a specific amount (e.g., 5 ul) required for the measuring the glycated hemoglobin is accurately collected.

Figure 9:
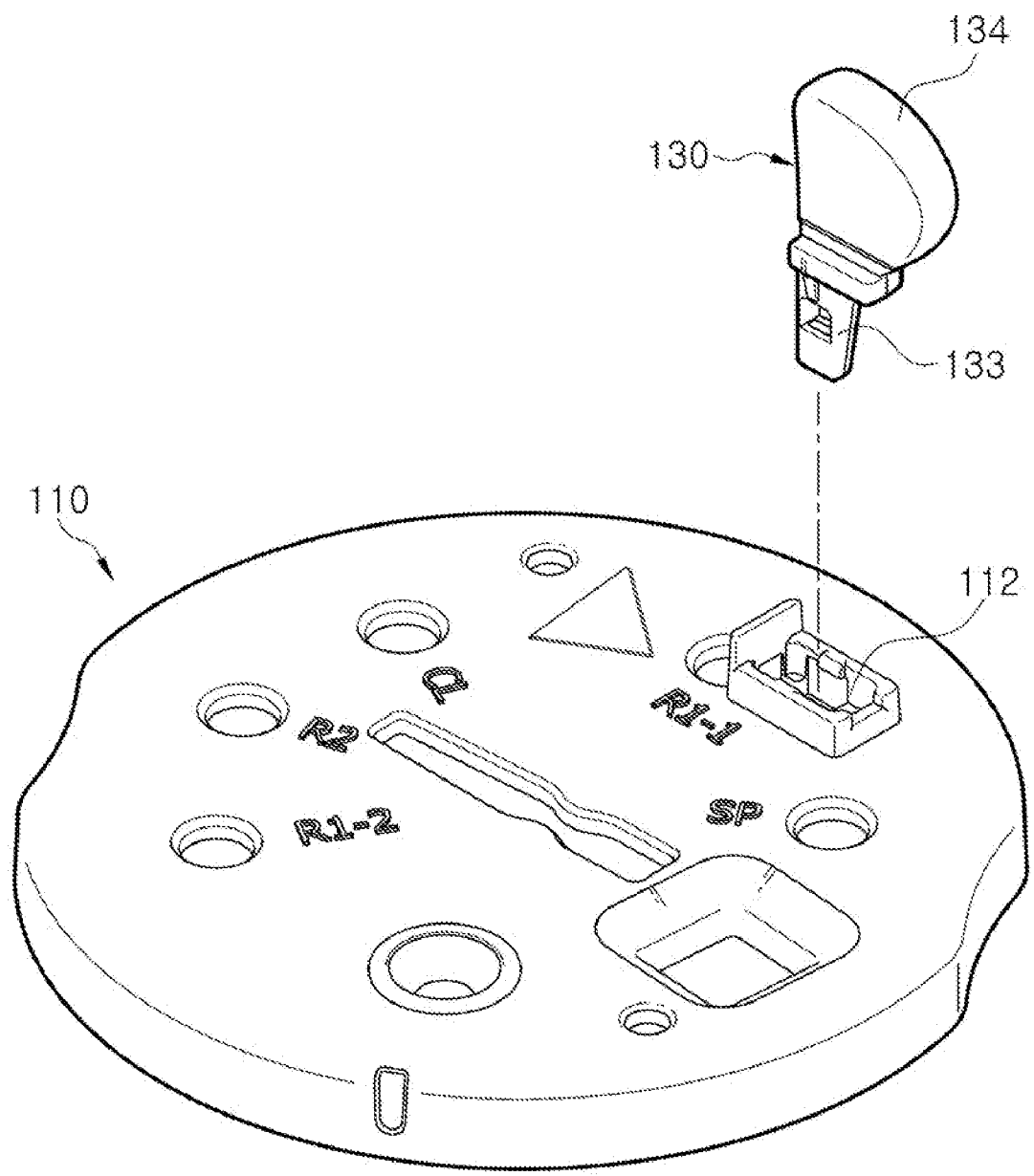
FIGS. 9, 10A, 10B, and 11 are views illustrating a cartridge and a capillary.
Figure 10A:
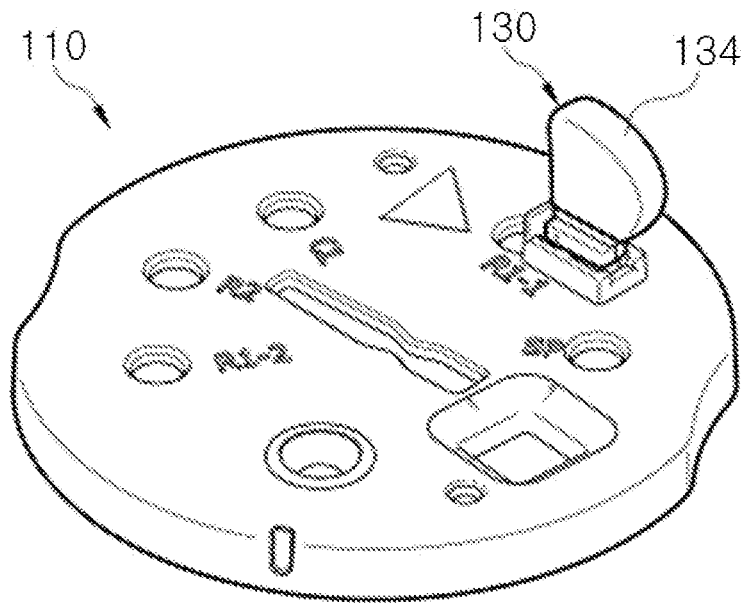
Figure 10B:
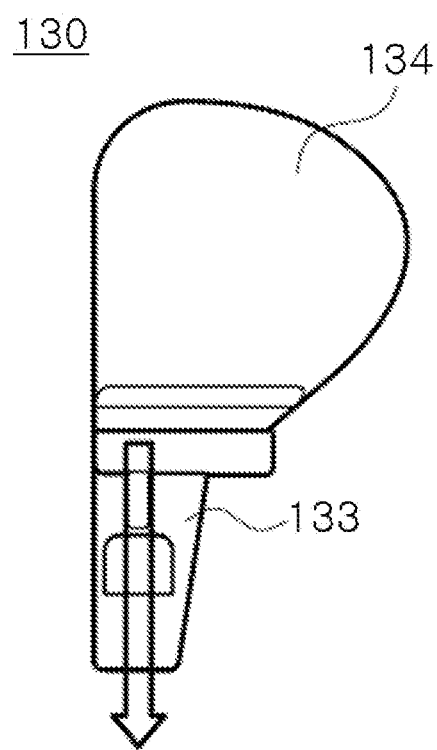

For example, the capillary 130 filled with the blood may be inserted into the capillary insertion hole 112 of the cartridge 100 as shown in FIG. 9. After being inserted as shown in FIG. 10A, the blood filled in the capillary receptacle 134 may be discharged into the blood receiving portion R1-1 of the cartridge 100 through the capillary insert 133 as shown in FIG. 10B. Thereafter, the capillary receptacle 134 may be separated from the capillary insert 133 by an external force of a person performing a test, and only the capillary insert 133 may be left in the cartridge 100. Therefore, the capillary receptacle 134 may not act as an element that hinders the rotation of the cartridge 100.

Figure 12:
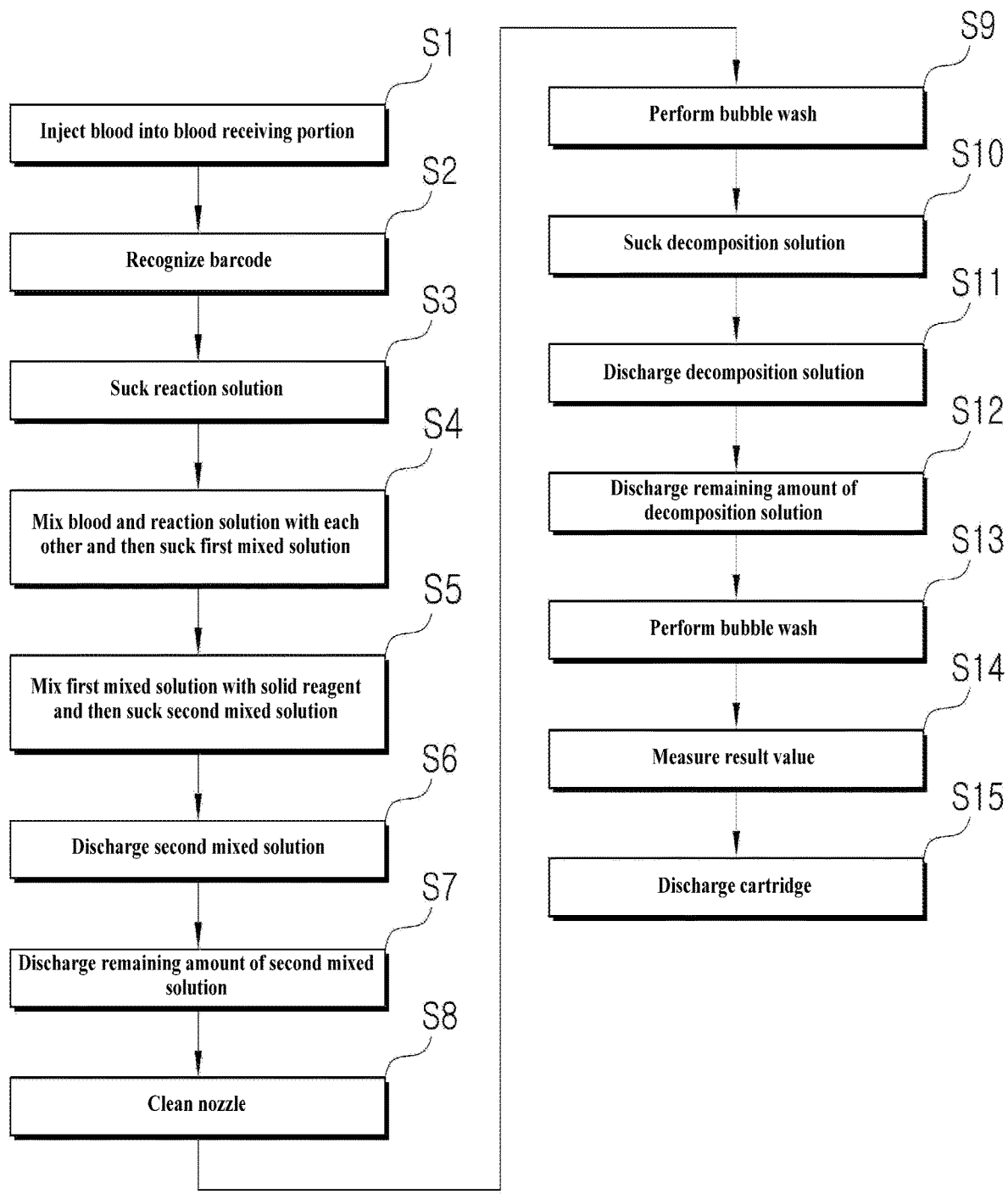
FIG. 12 is a flowchart illustrating a glycated hemoglobin measuring method using a glycated hemoglobin measuring apparatus according to an embodiment of the inventive concept.
Figure 13:
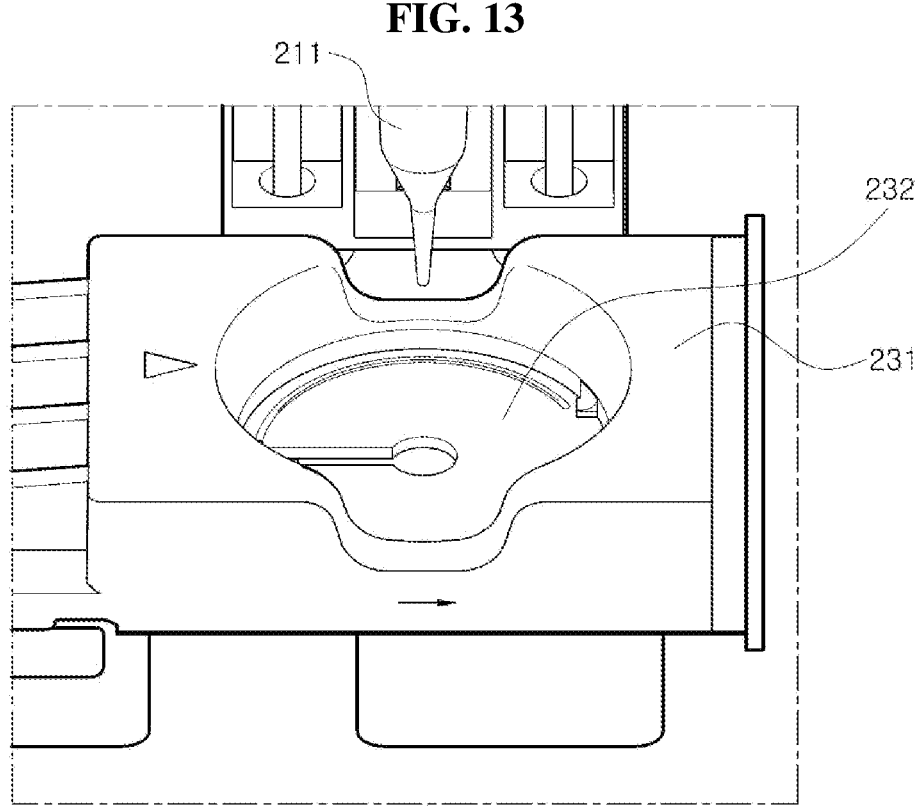
FIGS. 13 to 37 are exemplary views illustrating a glycated hemoglobin measuring method using a glycated hemoglobin measuring apparatus according to an embodiment of the inventive concept.

FIG. 12 is a flowchart illustrating a glycated hemoglobin measuring method using a glycated hemoglobin measuring apparatus according to an embodiment of the inventive concept. FIGS. 13 to 37 are exemplary views illustrating a glycated hemoglobin measuring method using a glycated hemoglobin measuring apparatus according to an embodiment of the inventive concept. Operations in FIG. 12 may be performed by each of the components of the glycated hemoglobin measuring apparatus 10 shown in FIGS. 1 to 2.

In one example, arrows indicated in each of the drawings respectively mean a moving direction of the nozzle 211 and a rotation direction of the cartridge 100 for moving from a current drawing to a next drawing. That is, when, for example, a downward arrow and a clockwise arrow are indicated in the current drawing, a direction of a next operation (the next drawing) of the nozzle 211 is a downward direction, and a rotation direction of a next operation (the next drawing) of the cartridge 100 may mean a clockwise direction.

Figure 11:
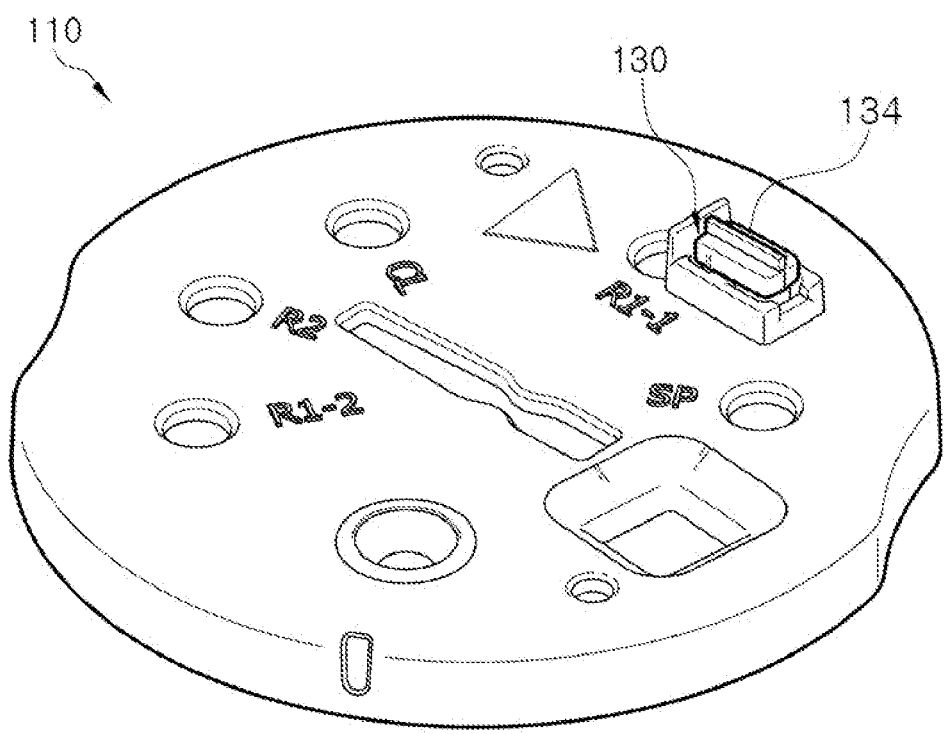

Referring to FIGS. 2 to 37, in an embodiment, in operation S1, the blood may be injected into the blood receiving portion R1-1 using the capillary 130 as shown in FIGS. 9 to 11. Operation S1 may be performed manually or may be performed automatically through a component such as a known robot arm. The cartridge 100 to be described below will be described on the assumption that the blood, the washing material, the solid reagent, the decomposition solution, the reaction solution, and the membrane are respectively contained in the blood receiving portion R1-1, the washing portion SP, the solid reagent receiving portion R1-2, the decomposition solution receiving portion R2, the reaction solution receiving portion CL, and the membrane receiving portion M.

In one example, in the present embodiment, the driver 210 may provide a desired amount by sucking a larger amount of a target material into the nozzle 211 than an amount to be provided, and then discarding the rest of the target material after providing the amount to be provided. That is, it is to prevent an occurrence of an error resulted from the remaining amount of the target material in the nozzle 211. Therefore, it is possible to make that next chemical sucking is unaffected by additionally performing the washing with the reaction solution of the reaction solution receiving portion CL.

Figure 14:
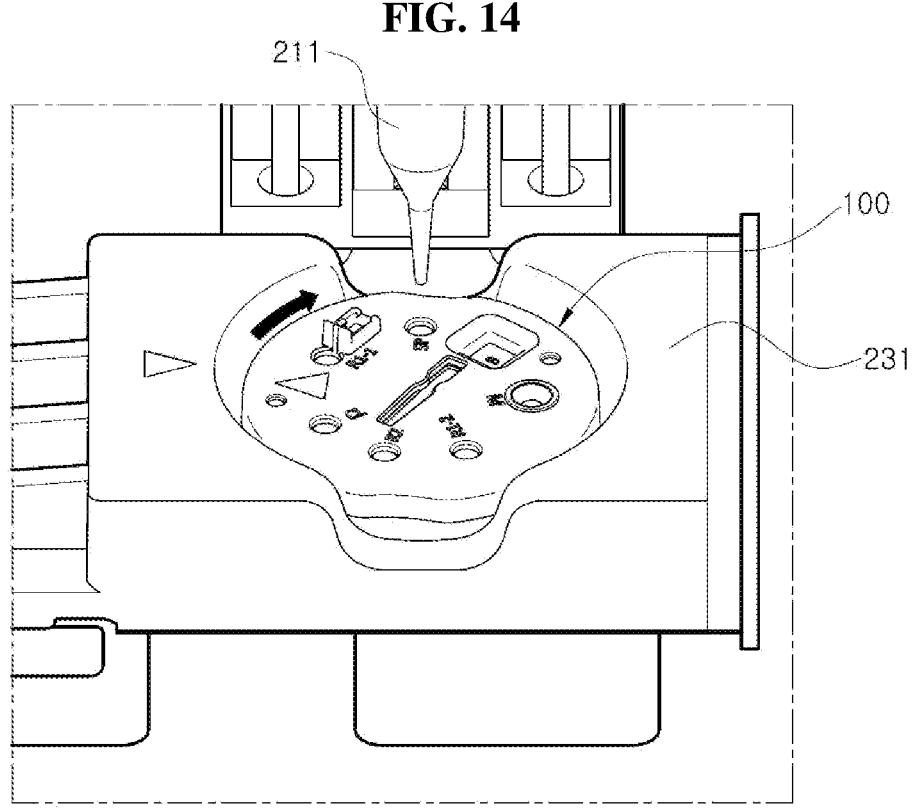
Figure 15:
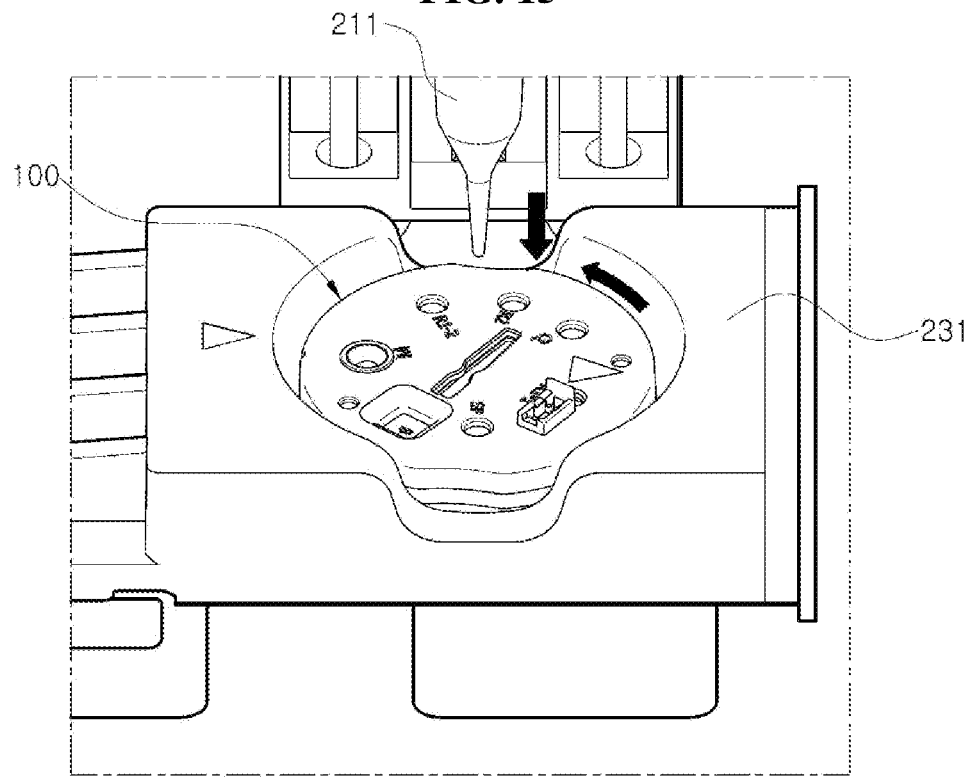

In an embodiment, in operation S2, the measurement unit 220 may recognize the information pattern sticker 150 placed in the information pattern recognition portion B of the cartridge 100. In this connection, the information pattern sticker 150 may include the barcode or the QR code. For example, as shown in FIG. 14, the cartridge 100 may be disposed in an empty space of the rotating tray body 231 shown in FIG. 13. This may be a case in which the cartridge 100 is inserted into the rotating tray body 231 based on a direction of the point sticker 140 (from right to left based on FIG. 14). For example, when the measurement unit 220 is located at 7 o'clock on the basis of the center of the cartridge 100 in FIG. 14 (all time directions to be described below are on the basis of the center of the cartridge 100), the rotating tray 230 may rotate the cartridge 100 by a preset angle in a counterclockwise direction as shown in FIG. 14. Accordingly, as shown in FIG. 15, a barcode portion may be located at 7 o'clock, and the measurement unit 220 may recognize the information pattern sticker 150 located in the barcode portion. For example, an algorithm may be preset to correct, by the driver 210, the error by acquiring information on the plurality of chemicals contained in the information pattern.

Figure 16:
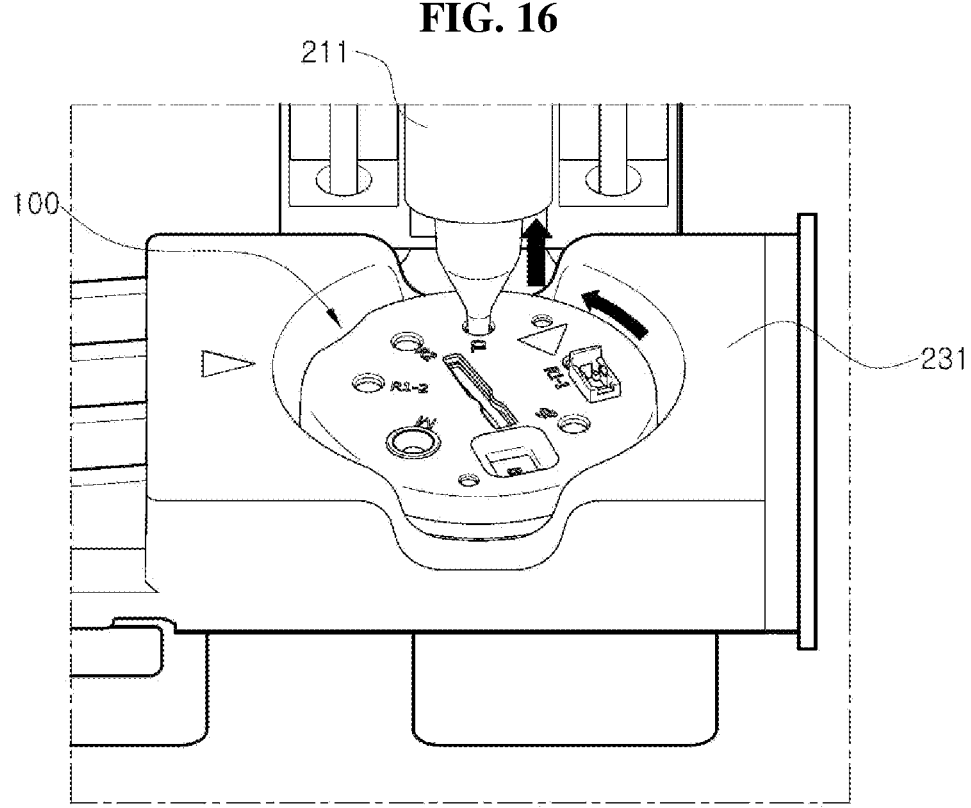

In an embodiment, in operation S3, the driver 210 may suck the reaction solution from the reaction solution receiving portion CL using the nozzle 211. First, in the present embodiment, the nozzle 211 will be described as being disposed at a fixed position at 12 o'clock. The rotating tray 230 may rotate the cartridge 100 in the counterclockwise direction as shown in FIG. 15 to position the reaction solution receiving portion CL below the nozzle 211 as shown in FIG. 16. The driver 210 may descend the nozzle 211 to the reaction solution receiving portion CL as shown in FIG. 15 to suck the reaction solution into the nozzle 211 as shown in FIG. 16. For example, 150 ul of the reaction solution may be sucked into the nozzle 211.

Figure 17:
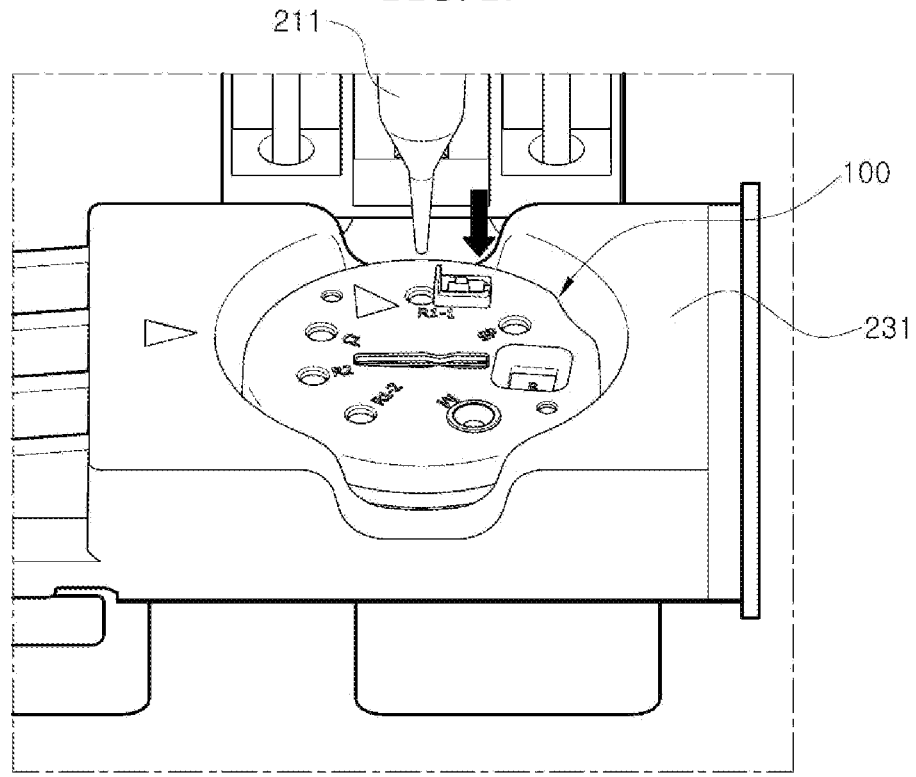
Figure 18:
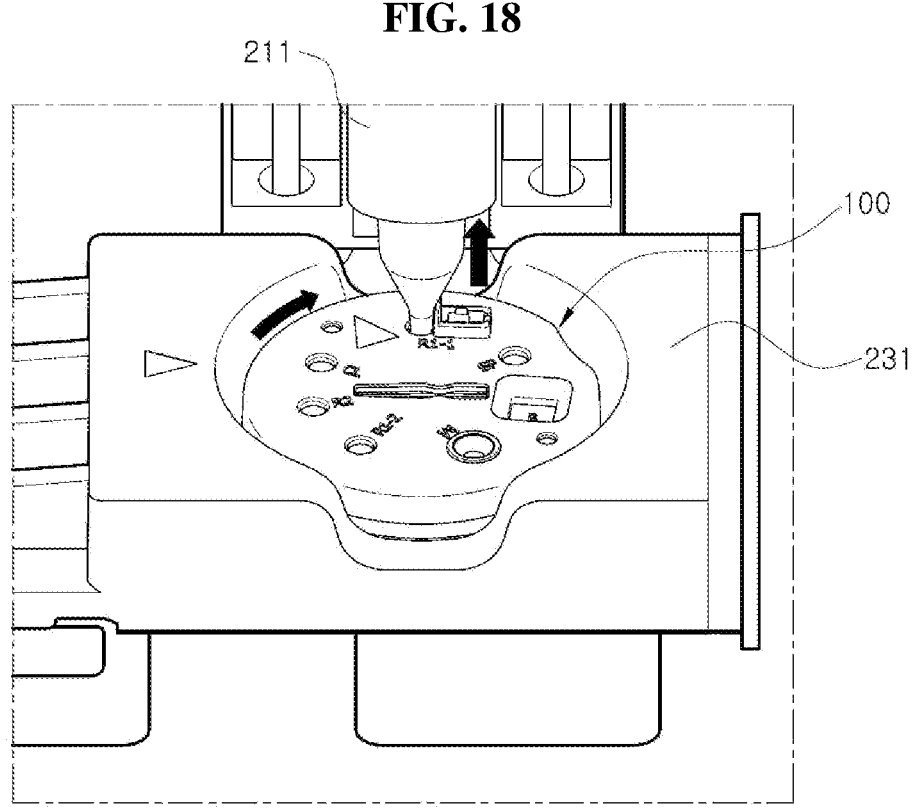

In an embodiment, in operation S4, after the blood and the reaction solution are mixed with each other in the blood receiving portion R1-1, the driver 210 may suck first mixed solution from the blood receiving portion R1-1 through the nozzle 211. For example, the driver 210 may ascend the nozzle 211 shown in FIG. 16 as shown in FIG. 17. The rotating tray 230 may rotate the cartridge 100 in the counterclockwise direction as shown in FIG. 16 to position the blood receiving portion R1-1 below the nozzle 211 as shown in FIG. 17. The driver 210 may descend the nozzle 211 to the blood receiving portion R1-1 as shown in FIG. 17 to discharge the sucked reaction solution into the blood receiving portion R1-1, and may descend the nozzle 211 to the blood receiving portion R1-1 as shown in FIG. 18 to suck the first mixed solution in which the discharged reaction solution and the blood are mixed with each other from the blood receiving portion R1-1. That is, for example, after 150 ul of the reaction solution is discharged into the blood receiving portion R1-1, and the blood and the reaction solution are mixed with each other, 150 ul, which is an entire amount, of the first mixed solution may be sucked into the nozzle 211.

Figure 19:
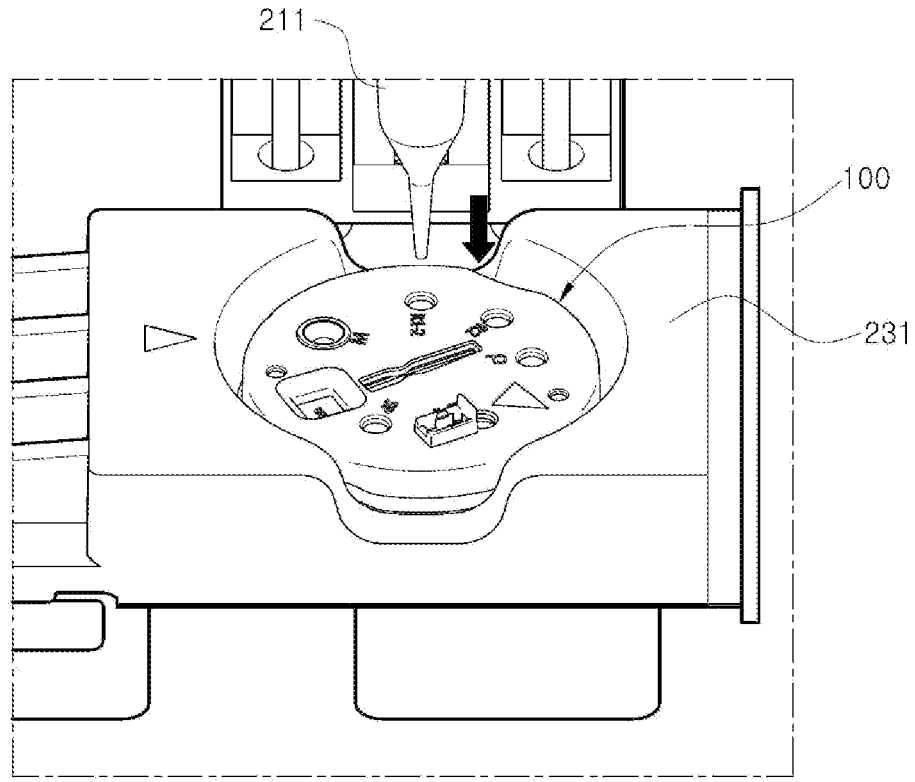
Figure 20:
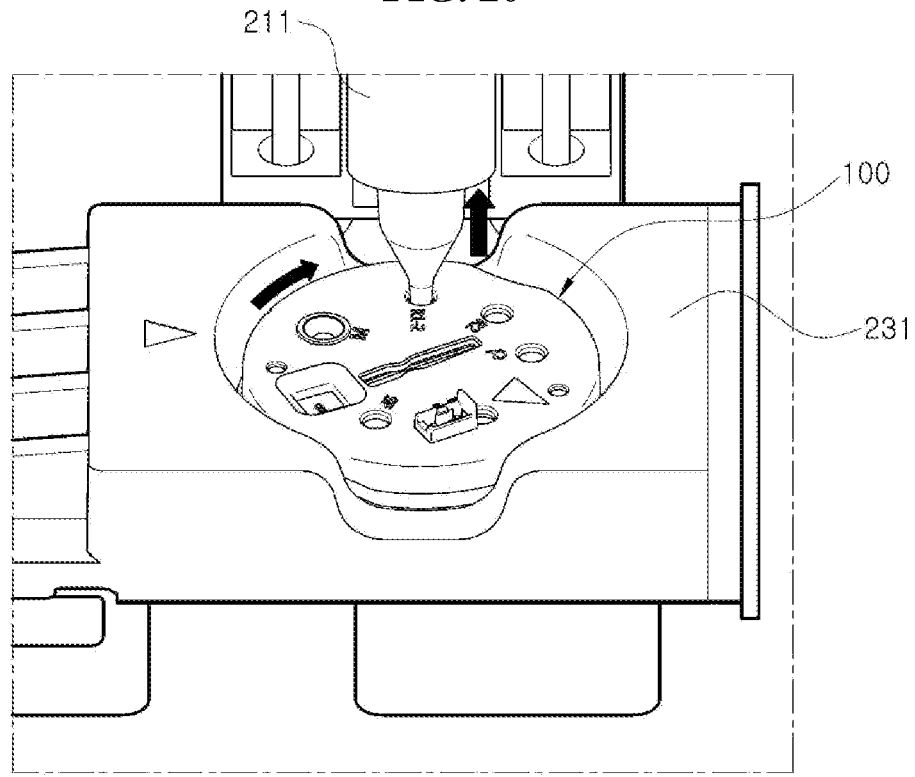

In an embodiment, in operation S5, after the first mixed solution and the solid reagent are mixed with each other in the solid reagent receiving portion R1-2, the driver 210 may suck second mixed solution from the solid reagent receiving portion R1-2 using the nozzle 211. For example, the driver 210 may ascend the nozzle 211 as shown in FIGS. 18 and 19. The rotating tray 230 may rotate the cartridge 100 in the clockwise direction as shown in FIG. 18 to position the solid reagent receiving portion R1-2 below the nozzle 211 as shown in FIG. 19. The driver 210 may descend the nozzle 211 to the solid reagent receiving portion R1-2 as shown in FIGS. 19 and 20 to discharge the sucked first mixed solution into the solid reagent receiving portion R1-2, and the driver 210 may descend the nozzle 211 to the solid reagent receiving portion R1-2 as shown in FIG. 20 to suck the second mixed solution in which the discharged first mixed solution and the solid reagent are mixed with each other into the nozzle 211 in the solid reagent receiving portion R1-2. For example, after discharging the entire amount of the first mixed solution into the solid reagent receiving portion R1-2, and mixing the first mixed solution and the solid reagent with each other, 100 ul of the second mixed solution may be sucked into the nozzle 211.

Figure 21:
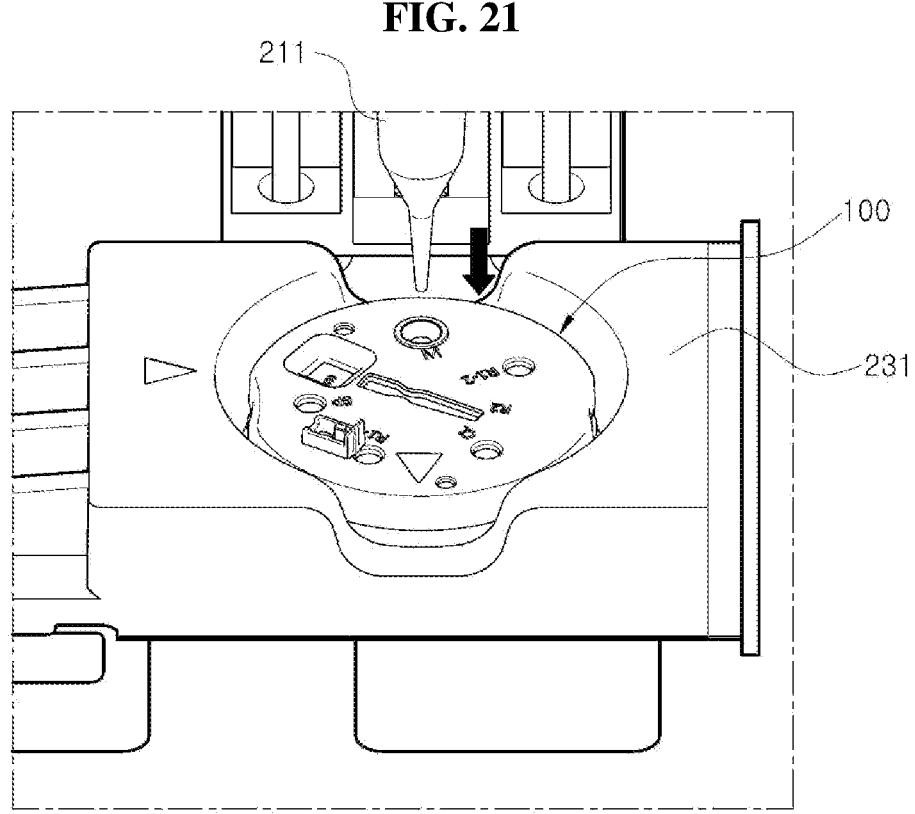
Figure 22:
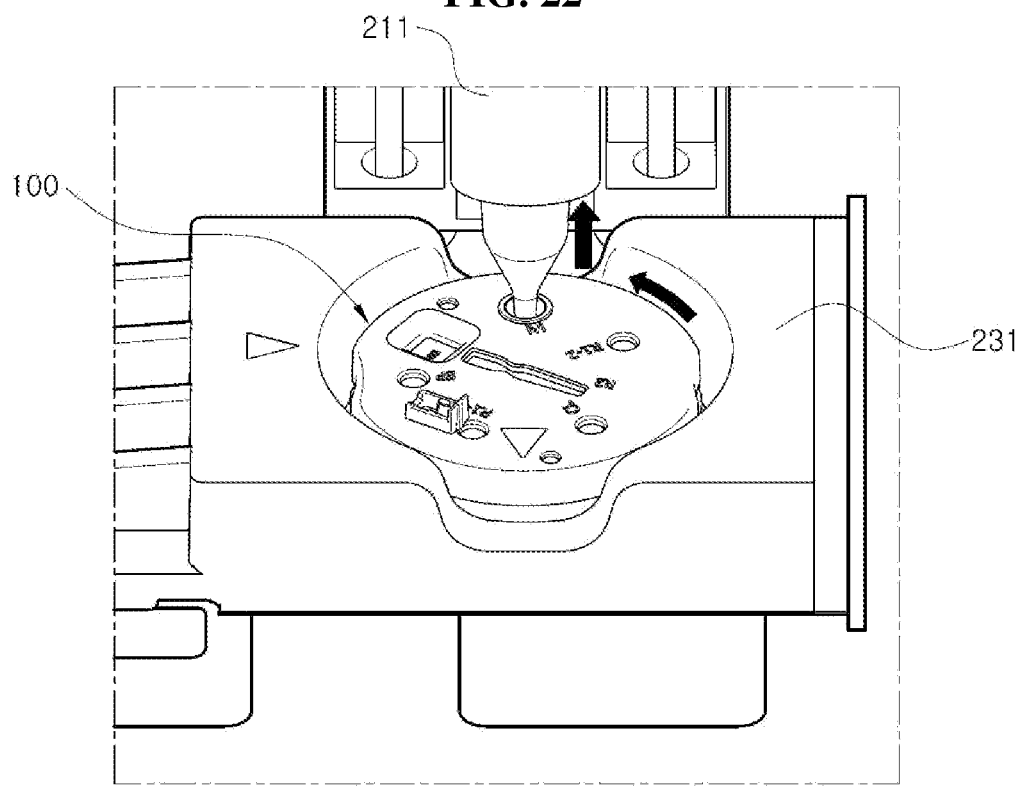

In an embodiment, in operation S6, the driver 210 may discharge the second mixed solution into the membrane receiving portion M using the nozzle 211. For example, the driver 210 may ascend the nozzle 211 again as shown in FIG. 20. The rotating tray 230 may rotate the cartridge 100 in the clockwise direction as shown in FIG. 20 to position the membrane receiving portion M below the nozzle 211 as shown in FIG. 21. The driver 210 may descend the nozzle 211 to the membrane receiving portion M as shown in FIGS. 21 and 22 to discharge a portion of the sucked second mixed solution into the membrane receiving portion M. For example, 25 ul of the second mixed solution may be discharged into the membrane receiving portion M.

Figure 23:
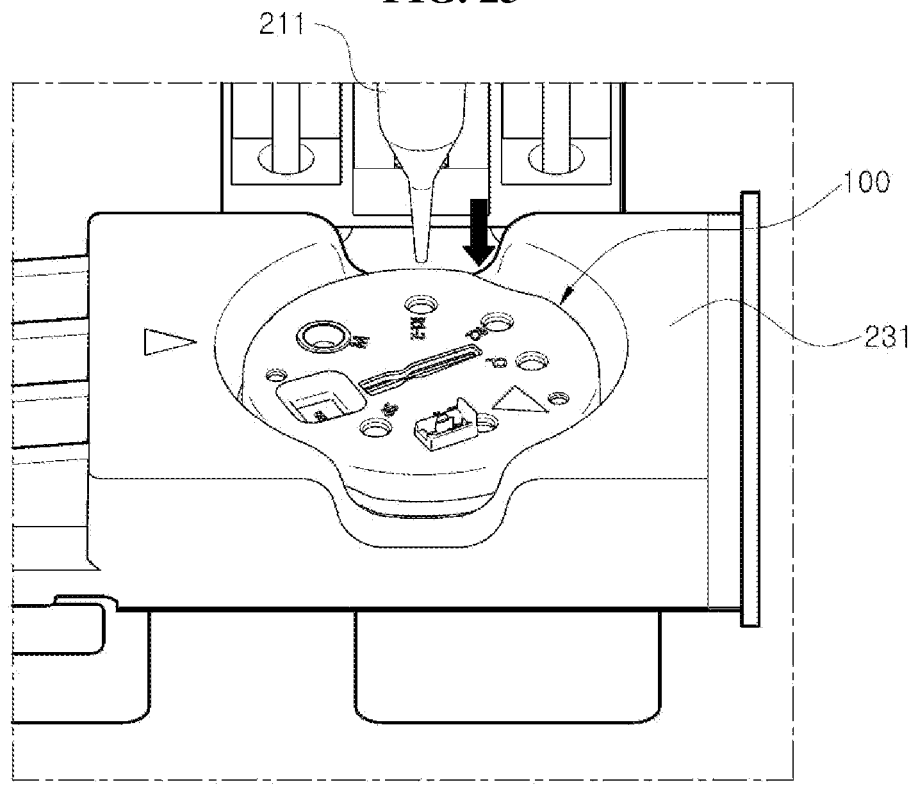
Figure 24:
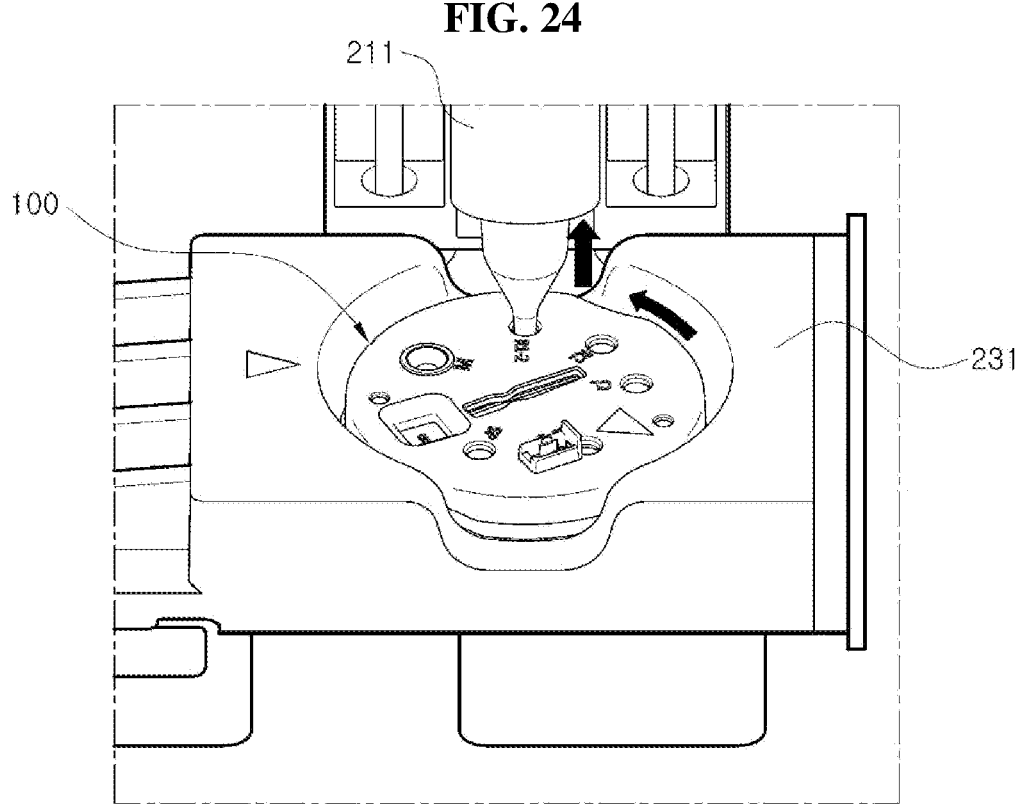

In an embodiment, in operation S7, the driver 210 may discharge a remaining amount of the second mixed solution into the solid reagent receiving portion R1-2 using the nozzle 211. For example, the driver 210 may ascend the nozzle 211 as shown in FIG. 22. The rotating tray 230 may rotate the cartridge 100 in the counterclockwise direction as shown in FIG. 22 to position the solid reagent receiving portion R1-2 below the nozzle 211 as shown in FIG. 23. The driver 210 may descend the nozzle 211 to the solid reagent receiving portion R1-2 as shown in FIGS. 23 and 24 to discharge the rest of the sucked second mixed solution into the solid reagent receiving portion R1-2. For example, 75 ul, which is the remaining amount, of the second mixed solution may be discharged into the solid reagent receiving portion R1-2.

Figure 25:
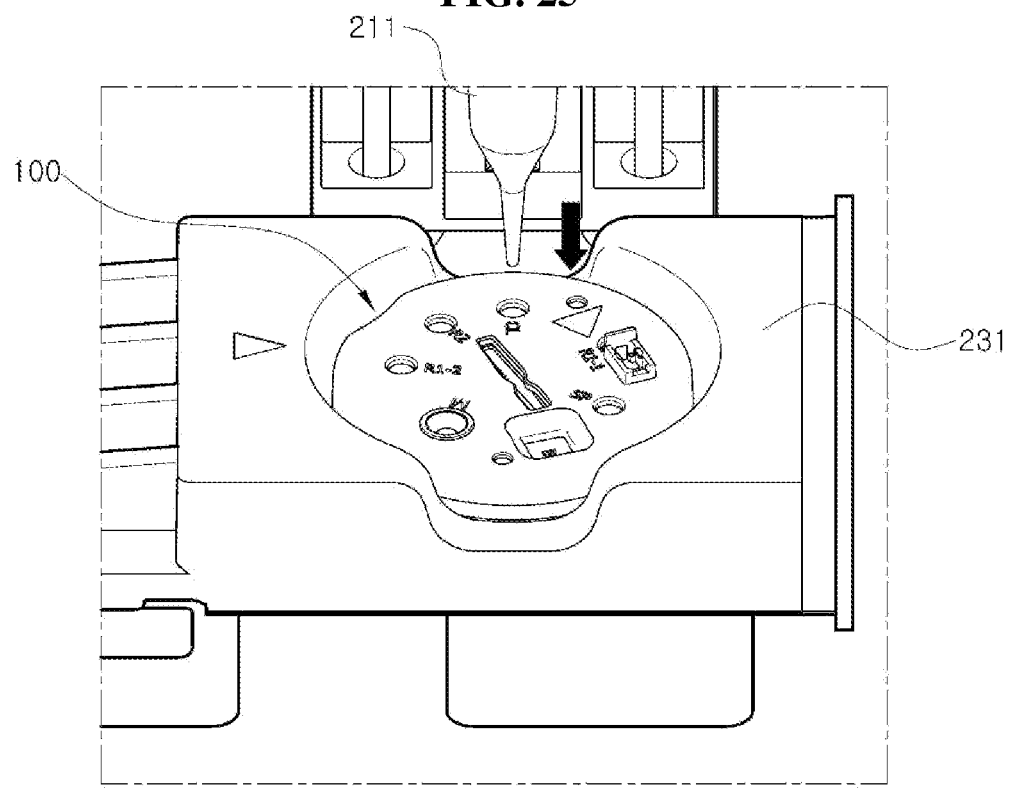
Figure 26:
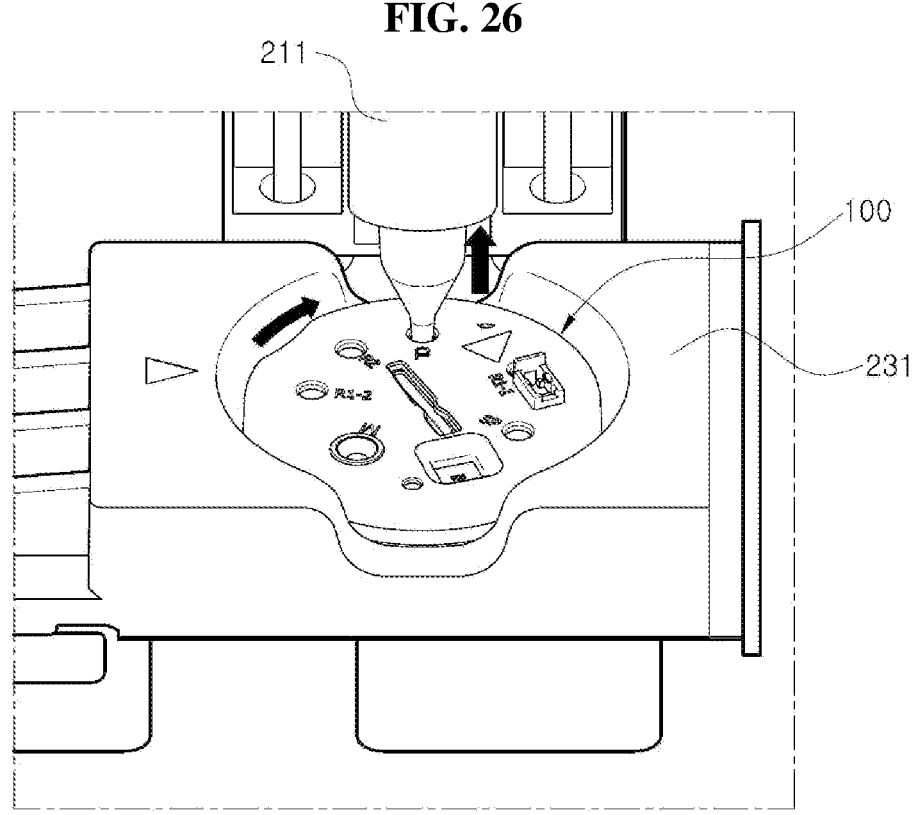

In an embodiment, in operation S8, the driver 210 may clean the nozzle 211 using the reaction solution in the reaction solution receiving portion CL. For example, the driver 210 may ascend the nozzle 211 as shown in FIG. 24. The rotating tray 230 may rotate the cartridge 100 in the counterclockwise direction as shown in FIG. 24 to position the reaction solution receiving portion CL below the nozzle 211 as shown in FIG. 25. The driver 210 may descend the nozzle 211 to the reaction solution receiving portion CL as shown in FIGS. 25 and 26 to wash the nozzle with the reaction solution.

Figure 27:
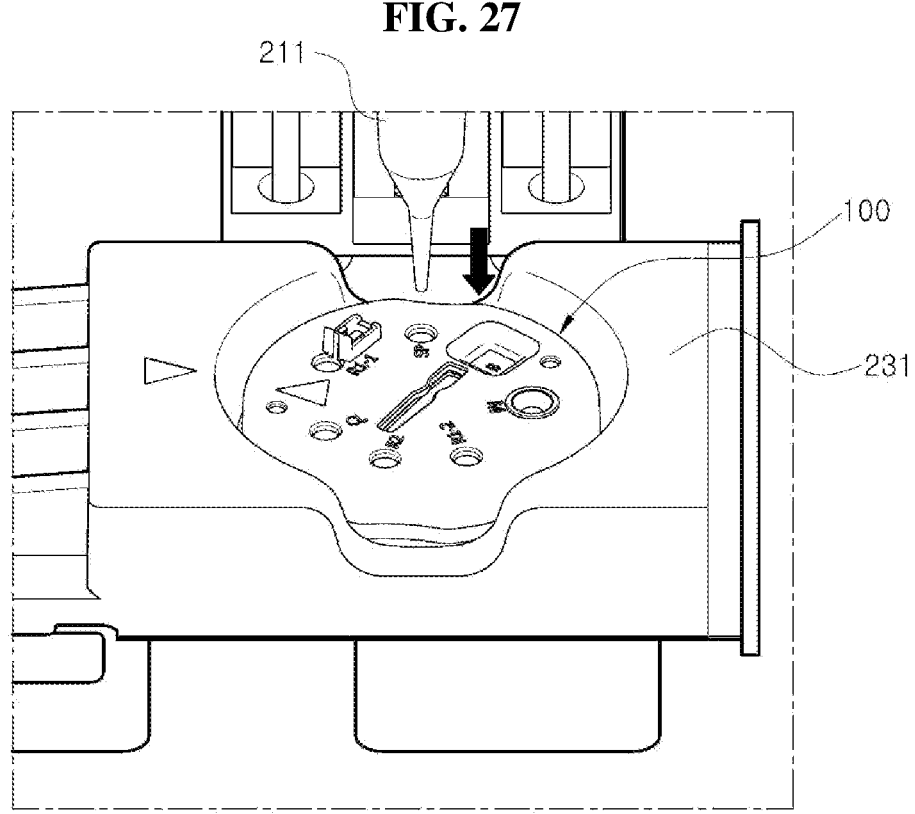
Figure 28:
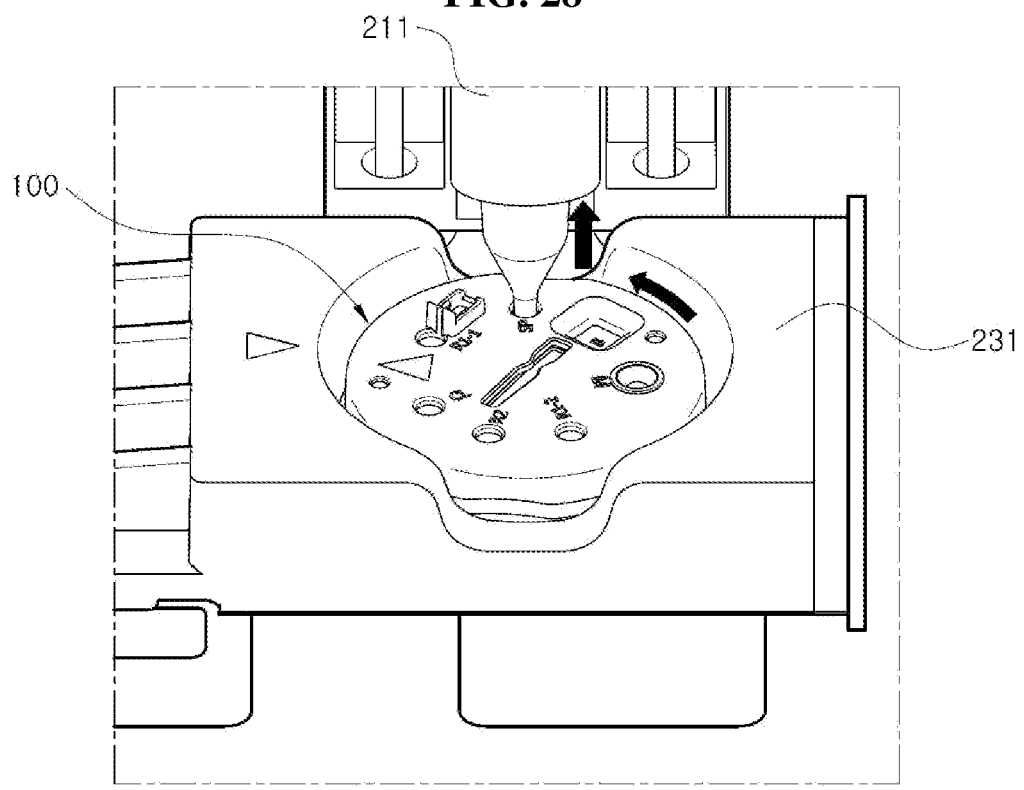

In an embodiment, in operation S9, the driver 210 may perform bubble wash on the nozzle 211 in the washing portion SP. For example, the driver 210 may ascend the nozzle 211 as shown in FIG. 26. The rotating tray 230 may rotate the cartridge 100 in the clockwise direction as shown in FIG. 26 to position the washing portion SP defined in the cartridge 100 below the nozzle 211 as shown in FIG. 27. The driver 210 may descend the nozzle 211 to the washing portion SP as shown in FIGS. 27 and 28 to wash the nozzle 211 with the washing material (e.g., a washing cotton) contained in the washing portion SP.

Figure 29:
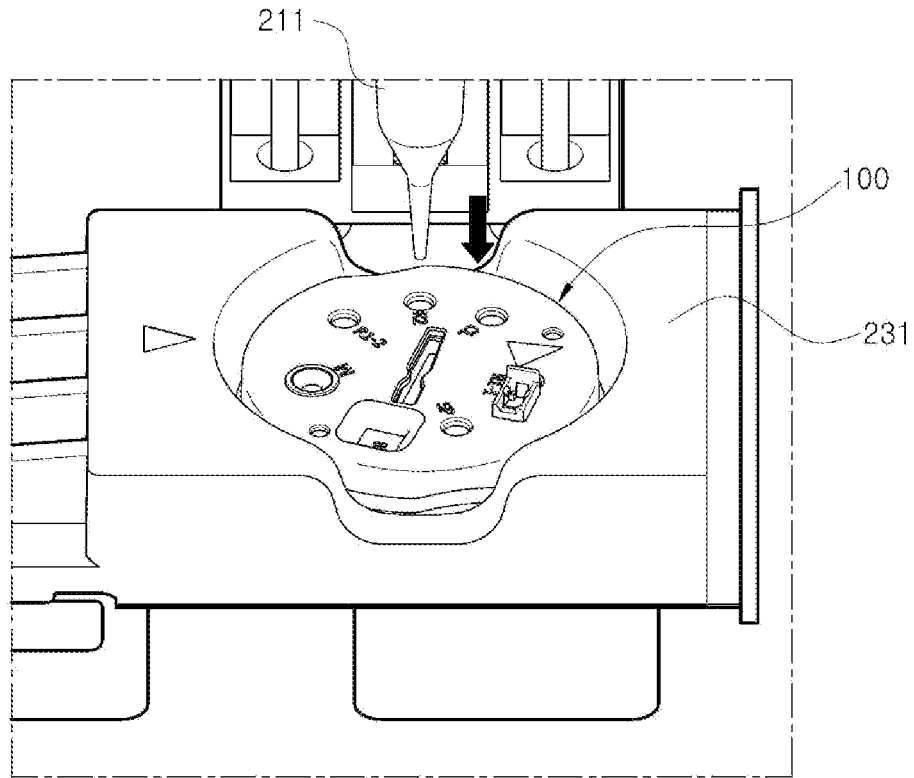
Figure 30:
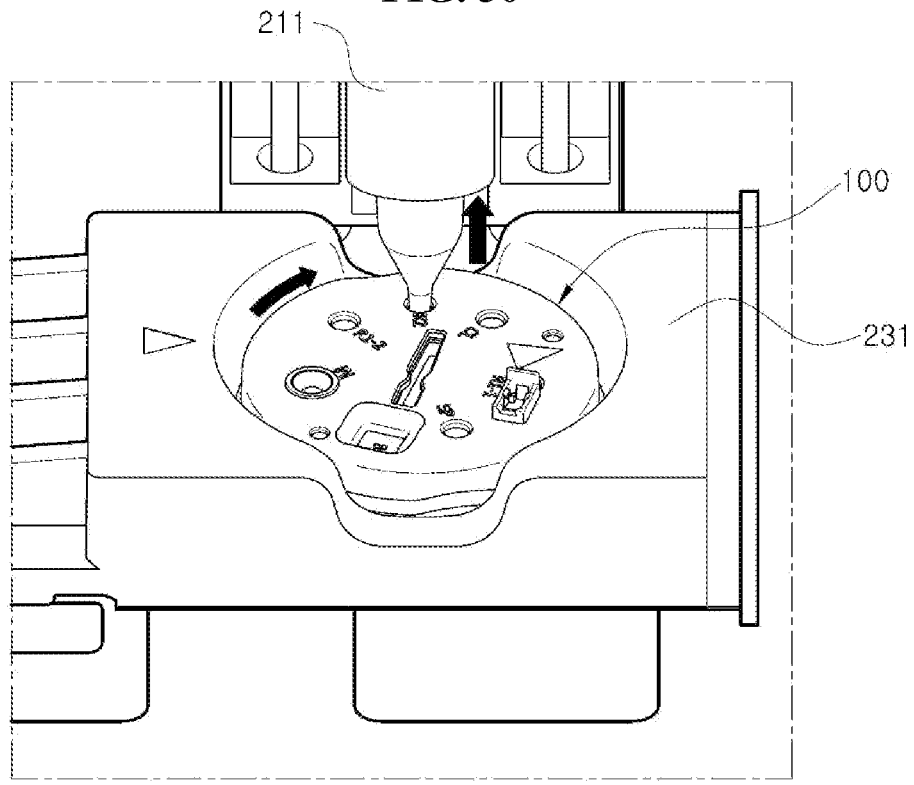

In an embodiment, in operation S10, the driver 210 may suck the decomposition solution from the decomposition solution receiving portion R2 using the nozzle 211. For example, the driver 210 may ascend the nozzle 211. The rotating tray 230 may rotate the cartridge 100 in the counterclockwise direction as shown in FIG. 28 to position the decomposition solution receiving portion R2 below the nozzle 211 as shown in FIG. 29. The driver 210 may descend the nozzle 211 to the decomposition solution receiving portion R2 as shown in FIGS. 29 and 30 to suck the decomposition solution into the nozzle 211. For example, 100 ul of the decomposition solution may be sucked into the nozzle 211.

Figure 31:
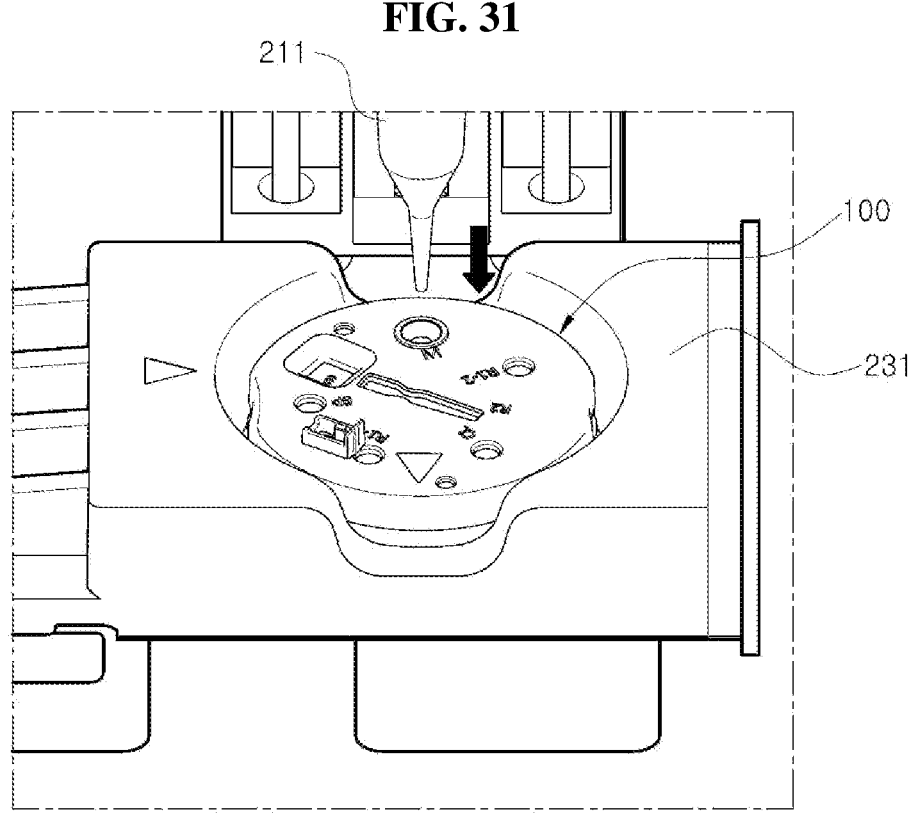
Figure 32:
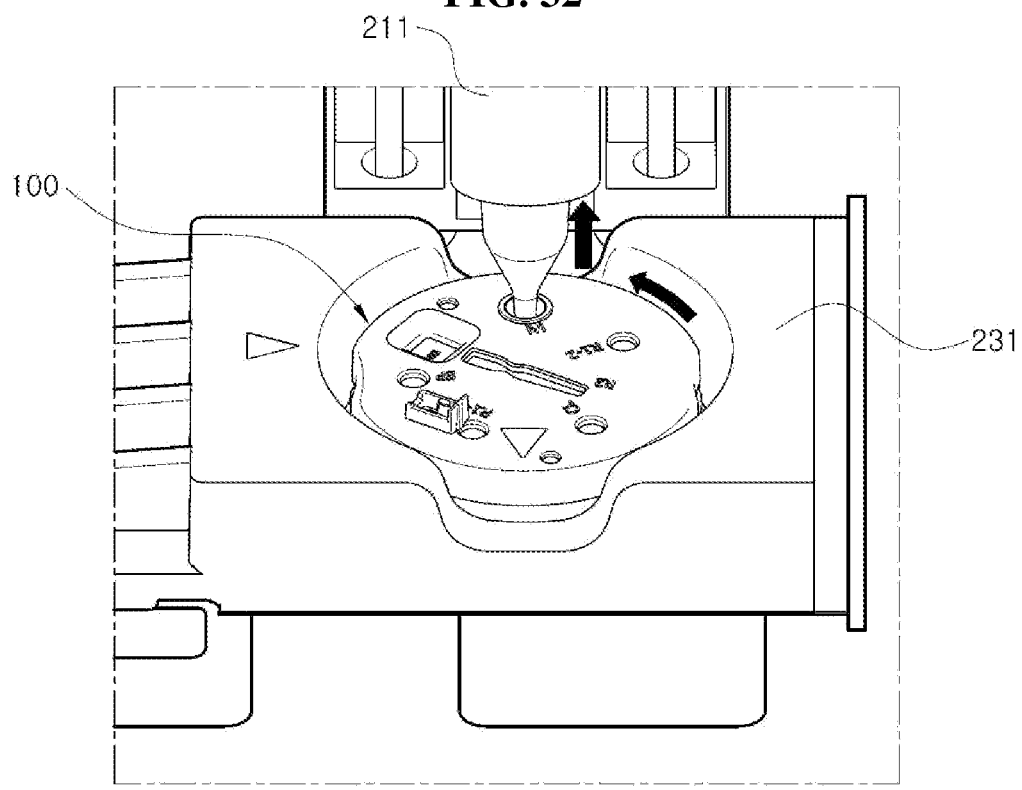

In an embodiment, in operation S11, the driver 210 may discharge the decomposition solution into the membrane receiving portion M using the nozzle 211. For example, the driver 210 may ascend the nozzle 211 as shown in FIGS. 30 and 31. The rotating tray 230 may rotate the cartridge 100 in the clockwise direction as shown in FIG. 30 to position the membrane receiving portion M below the nozzle 211 as shown in FIG. 31. The driver 210 may descend the nozzle 211 to the membrane receiving portion M as shown in FIGS. 31 and 32 to discharge a portion of the sucked decomposition solution into the membrane receiving portion M. For example, 25 ul of the decomposition solution may be discharged into the membrane receiving portion M.

Figure 33:
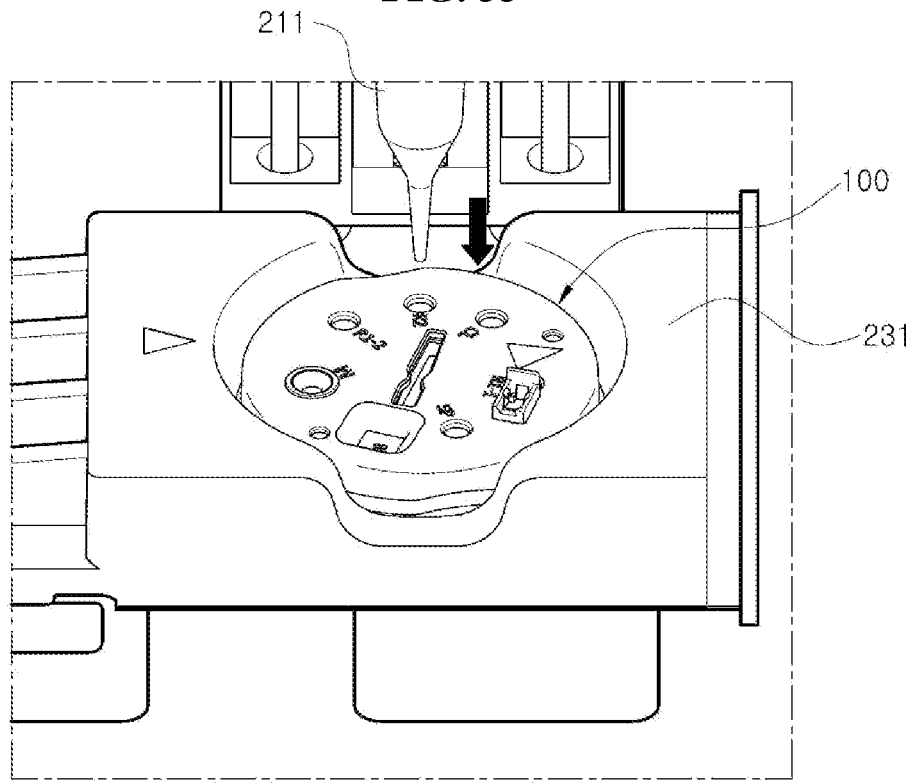
Figure 34:
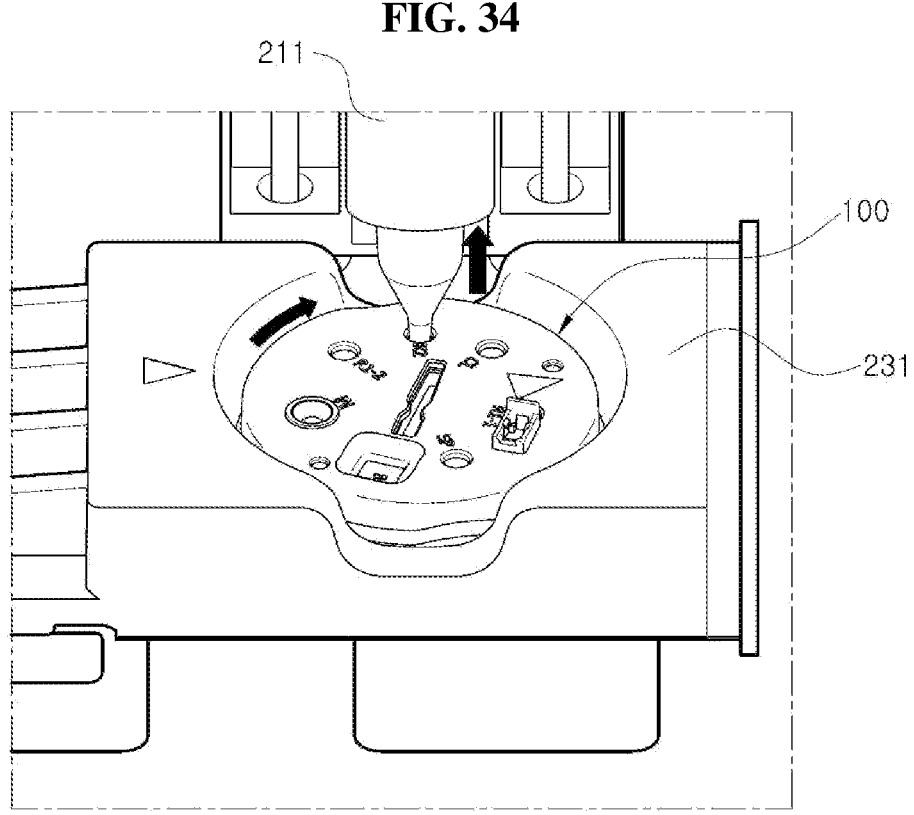

In an embodiment, in operation S12, the driver 210 may discharge a remaining amount of the decomposition solution into the decomposition solution receiving portion R2 using the nozzle 211. For example, the driver 210 may ascend the nozzle 211 as shown in FIGS. 32 and 33. The rotating tray 230 may rotate the cartridge 100 in the counterclockwise direction as shown in FIG. 32 to position the decomposition solution receiving portion R2 below the nozzle 211 as shown in FIG. 33. The driver 210 may descend the nozzle 211 to the decomposition solution receiving portion R2 as shown in FIGS. 33 and 34 to discharge the rest of the sucked decomposition solution into the decomposition solution receiving portion R2. For example, 75 ul, which is the remaining amount, of the decomposition solution may be discharged into the decomposition solution receiving portion R2.

Figure 35:
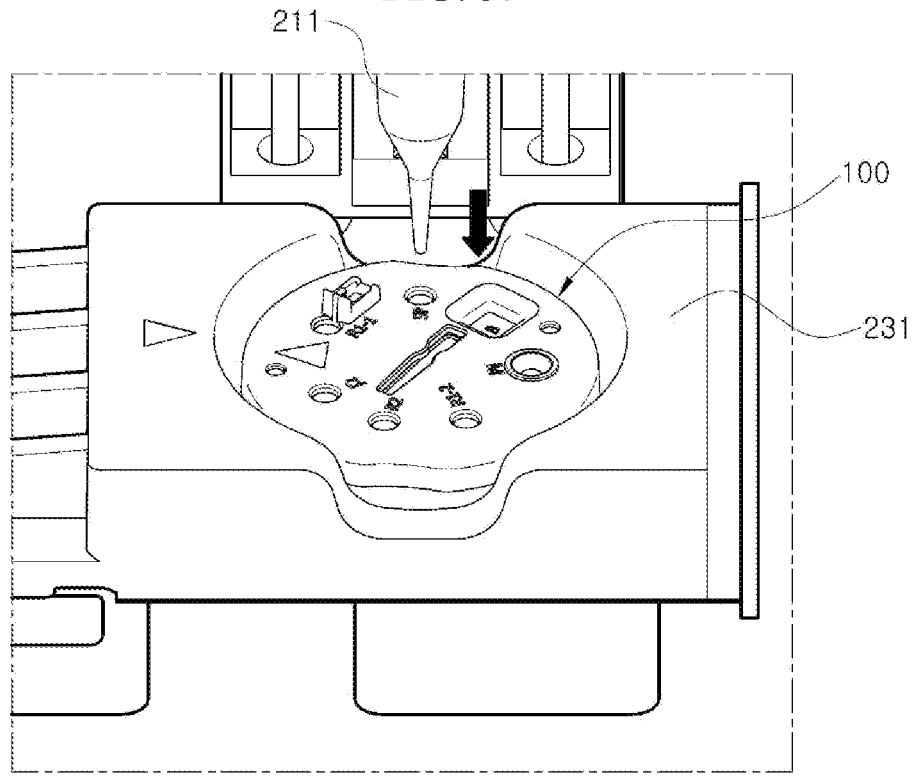
Figure 36:
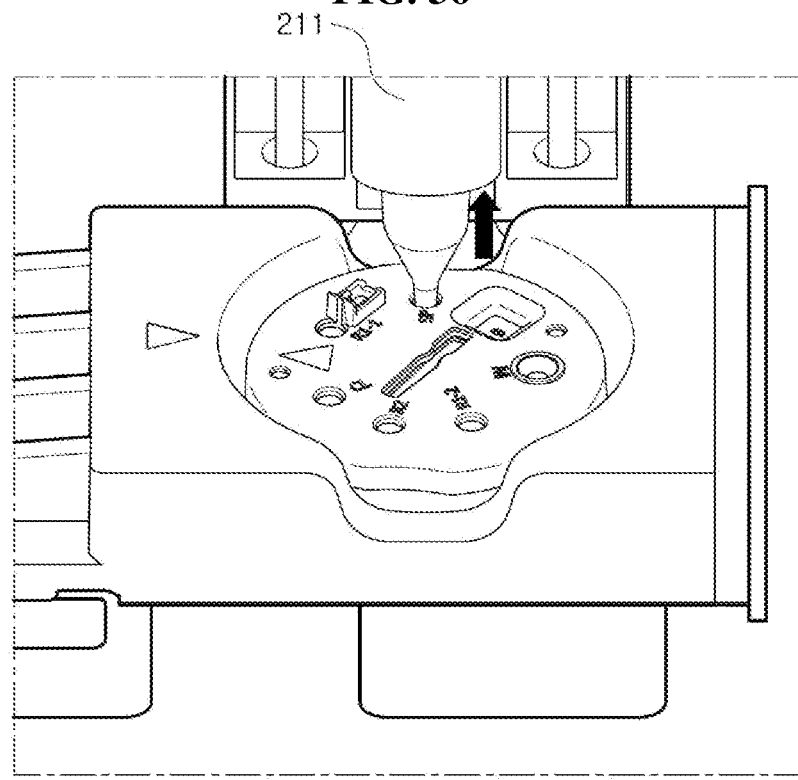

In an embodiment, in operation S13, the driver 210 may perform the bubble wash on the nozzle 211 in the washing portion SP. For example, the driver 210 may ascend the nozzle 211 as shown in FIGS. 34 and 35. The rotating tray 230 may rotate the cartridge 100 in the clockwise direction as shown in FIG. 34 to position the washing portion SP defined in the cartridge 100 below the nozzle 211 as shown in FIG. 35. The driver 210 may descend the nozzle 211 to the washing portion SP as shown in FIGS. 35 and 36 to wash the nozzle 211 with the washing material (e.g., the washing cotton) contained in the washing portion SP.

Figure 37:
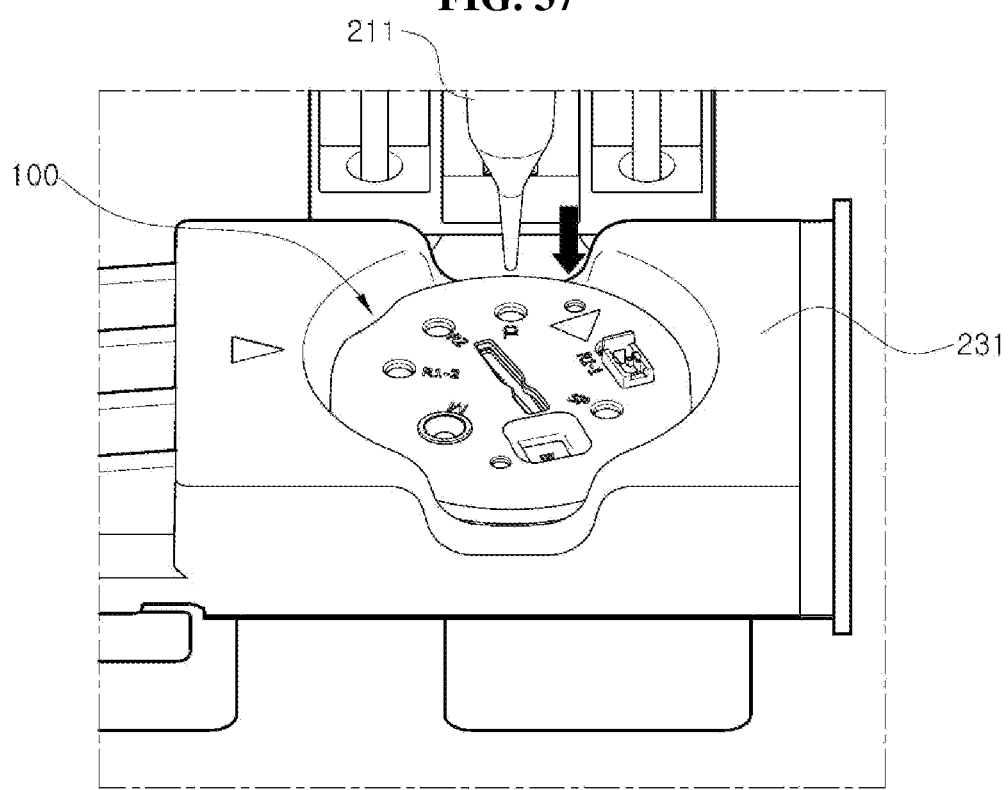

In an embodiment, in operation S14, the measurement unit 220 may measure a result value in the membrane receiving portion M. For example, the driver 210 may ascend the nozzle 211 as shown in FIGS. 36 and 37. The rotating tray 230 may rotate the cartridge 100 in the clockwise direction as shown in FIGS. 36 and 37 to position the membrane receiving portion M in a region (at 7 o'clock) where the measurement unit 220 may perform the measurement. The measurement unit 220 may acquire the result value by measuring the glycated hemoglobin from third mixed solution in which the second mixed solution and the decomposition solution contained in the membrane receiving portion M are mixed with each other.

In an embodiment, in operation S15, the driver 210 may discharge the cartridge 100. For example, the rotating tray 230 may expose the rotating tray body 231 to the outside along the guide 233 as shown in FIG. 1. Accordingly, the cartridge 100 exposed to the outside may be withdrawn.

In this way, the blood may be automatically chemically treated and the glycated hemoglobin may be measured by simply inserting the cartridge 100 filled with the blood and the plurality of chemicals into the glycated hemoglobin apparatus 10.

An apparatus for measuring glycated hemoglobin according to an embodiment of the inventive concept may include a cartridge for receiving blood and a plurality of chemicals, a rotating tray for rotating the cartridge, wherein the cartridge is disposed inside the rotating tray, a driver having a nozzle disposed above the cartridge and movable in a vertical direction, and a measurement unit located above the cartridge and measuring glycated hemoglobin of the blood. The driver may suck at least one of the blood, the plurality of chemicals, and mixed solution of the blood and the plurality of chemicals into the nozzle or discharge the sucked at least one into the cartridge such that the blood is chemically treated through the plurality of chemicals.

According to various embodiments, the plurality of chemicals may include solid reagent, decomposition solution, and reaction solution. The cartridge may include a blood receiving portion for receiving the blood, a solid reagent receiving portion for receiving the solid reagent, a decomposition solution receiving portion for receiving the decomposition solution, a reaction solution receiving portion for receiving the reaction solution, and a membrane receiving portion for receiving a membrane.

According to various embodiments, the rotating tray may rotate the cartridge based on a preset angle such that the blood receiving portion, the solid reagent receiving portion, the decomposition solution receiving portion, the reaction solution receiving portion, or the membrane receiving portion is located in a region where the nozzle moves in the vertical direction.

According to various embodiments, the cartridge may include an upper cartridge including a blood receiving hole for exposing the blood to an outside such that the nozzle is able to pass through the blood receiving hole, a solid reagent receiving hole for exposing the solid reagent to the outside, a decomposition solution receiving hole for exposing the decomposition solution to the outside, a reaction solution receiving hole for exposing the reaction solution to the outside, and a membrane receiving hole for exposing the membrane to the outside, and a lower cartridge including a blood receiving receptacle for receiving the blood, a solid reagent receiving receptacle for receiving the solid reagent, a decomposition solution receiving receptacle for receiving the decomposition solution, a reaction solution receiving receptacle for receiving the reaction solution, and a membrane receiving receptacle for receiving the membrane.

According to various embodiments, the cartridge may further include a sealing member for covering the solid reagent receiving receptacle, the decomposition solution receiving receptacle, and the reaction solution receiving receptacle to prevent leakage of the solid reagent, the decomposition solution, and the reaction solution, and a container inserted into the solid reagent receiving receptacle to receive the solid reagent.

According to various embodiments, the cartridge may further include a capillary for storing the blood in advance and seated in a groove defined in the upper cartridge. The capillary may include a capillary insert capable of being inserted into a capillary insertion hole defined in the upper cartridge and in communication with the blood receiving receptacle, and a capillary receptacle connected to the capillary insert to be detachable by an external force and receiving the blood stored in advance.

According to various embodiments, the cartridge may further include a washing portion provided with a material for washing the nozzle, an information pattern recognition portion, wherein an information pattern sticker including information related to the plurality of chemicals is disposed in the information pattern recognition portion, and a point sticker portion, wherein a point sticker indicating an insertion direction of the cartridge into the rotating tray is disposed in the point sticker portion.

A method for measuring glycated hemoglobin using the apparatus for measuring the glycated hemoglobin of claim 2 according to an embodiment of the inventive concept may include rotating, by a rotating tray, a cartridge to position a reaction solution receiving portion below a nozzle, descending, by a driver, the nozzle to the reaction solution receiving portion to suck reaction solution into the nozzle, rotating, by the rotating tray, the cartridge to position a blood receiving portion below the nozzle, descending, by the driver, the nozzle to the blood receiving portion to discharge the sucked reaction solution into the blood receiving portion, descending, by the driver, the nozzle to the blood receiving portion to suck first mixed solution of the discharged reaction solution and blood into the nozzle from the blood receiving portion, rotating, by the rotating tray, the cartridge to position a solid reagent receiving portion below the nozzle, descending, by the driver, the nozzle to the solid reagent receiving portion to discharge the sucked first mixed solution into the solid reagent receiving portion, descending, by the driver, the nozzle to the solid reagent receiving portion to suck second mixed solution of the discharged first mixed solution and solid reagent into the nozzle from the solid reagent receiving portion, rotating, by the rotating tray, the cartridge to position a membrane receiving portion below the nozzle, and descending, by the driver, the nozzle to the membrane receiving portion to discharge a portion of the sucked second mixed solution into the membrane receiving portion.

According to various embodiments, the method may further include rotating, by the rotating tray, the cartridge to position the solid reagent receiving portion below the nozzle, descending, by the driver, the nozzle to the solid reagent receiving portion to discharge the rest of the sucked second mixed solution into the solid reagent receiving portion, rotating, by the rotating tray, the cartridge to position the reaction solution receiving portion below the nozzle, descending, by the driver, the nozzle to the reaction solution receiving portion to wash the nozzle with the reaction solution, rotating, by the rotating tray, the cartridge to position a washing portion defined in the cartridge below the nozzle, and descending, by the driver, the nozzle to the washing portion to wash the nozzle with a washing material contained in the washing portion.

According to various embodiments, the method may further include rotating, by the rotating tray, the cartridge to position a decomposition solution receiving portion below the nozzle, descending, by the driver, the nozzle to the decomposition solution receiving portion to suck decomposition solution into the nozzle, rotating, by the rotating tray, the cartridge to position the membrane receiving portion below the nozzle, descending, by the driver, the nozzle to the membrane receiving portion to discharge a portion of the sucked decomposition solution into the membrane receiving portion, rotating, by the rotating tray, the cartridge to position the decomposition solution receiving portion below the nozzle, descending, by the driver, the nozzle to the decomposition solution receiving portion to discharge the rest of the sucked decomposition solution into the decomposition solution receiving portion, rotating, by the rotating tray, the cartridge to position the membrane receiving portion in a region where the measurement is able to be performed by a measurement unit, and measuring, by the measurement unit, glycated hemoglobin from third mixed solution of the second mixed solution and the decomposition solution received in the membrane receiving portion.

According to the inventive concept as described above, there are various effects as follows.

According to the inventive concept, because the plurality of operations that must be taken to measure the glycated hemoglobin are performed automatically instead of manually, the glycated hemoglobin may be more conveniently and quickly measured.

In addition, according to the inventive concept, because an information pattern that may minimize the error occurring in the glycated hemoglobin measurement process is used, the glycated hemoglobin may be measured more accurately.

The effects of the inventive concept are not limited to the effects mentioned above, and other effects that are not mentioned will be clearly understood by those skilled in the art from the following description.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An apparatus for measuring glycated hemoglobin, the apparatus comprising:
    an apparatus body:
    a cartridge connected to the apparatus body, the cartridge comprising:
        an upper cartridge,
        a lower cartridge,
        a plurality of cartridge receptacles connected to the lower cartridge; and
        a capillary insertion hole on the upper cartridge,
        wherein the plurality of cartridge receptacles comprise:
            a first cartridge receptacle configured to receive and store blood; and
            a plurality of second cartridge receptacles configured to store a plurality of chemicals, and
        wherein the capillary insertion hole is connected with the first cartridge receptacle;
    a capillary connected to the upper cartridge, the capillary comprising:
        a capillary receptacle configured to store the blood; and
        a capillary insert configured to:
            be inserted into the capillary insertion hole of the cartridge
            receive the blood from the capillary receptacle; and
            discharge the blood to the first cartridge receptacle of the cartridge
    a rotating tray connected to the apparatus body, said rotating tray configured to rotate the cartridge, wherein the cartridge is positioned inside the rotating tray;
    a driver connected to the apparatus body, said driver having a nozzle wherein the nozzle is positioned above the cartridge and configured to move in a vertical direction; and
    a measurement unit connected to the apparatus body, said measurement unit positioned above the cartridge and configured to measure glycated hemoglobin of the blood,
    wherein the driver is configured to:
        suck the blood and the plurality of chemicals via the nozzle, from the cartridge, such that the blood is chemically treated through the plurality of chemicals; and
        discharge the blood that has been chemically treated through the plurality of chemicals, to the cartridge, via the nozzle.

2. The apparatus of claim 1, wherein the plurality of chemicals comprise solid reagent, decomposition solution, and reaction solution, and
    wherein the plurality of second cartridge receptacles comprise:
    a solid reagent receiving receptacle configured to store the solid reagent;
    a decomposition solution receiving receptacle configured to store the decomposition solution; and
    a reaction solution receiving receptacle configured to store the reaction solution, and
    wherein the plurality of cartridge receptacles further comprise a membrane receiving receptacle configured to store a membrane.

3. The apparatus of claim 1, wherein the rotating tray is configured to rotate the cartridge based on a preset angle, such that one of the plurality of cartridge receptacles is positioned where the nozzle moves in the vertical direction.

4. The apparatus of claim 1, wherein each cartridge receptacle of the plurality of cartridge receptacles has an opening in which the nozzle is configured to be inserted.

5. The apparatus of claim 2, wherein the cartridge further comprises
    a sealing member attached to, and covering the opening of the plurality of second cartridge receptacles to prevent leakage from the plurality of second cartridge receptacles and,
    a container inserted into the solid reagent receiving receptacle and configured to receive the solid reagent.

6. The apparatus of claim 4, wherein the cartridge further comprises:
    a washing portion hole that stores a material for washing the nozzle;

an information groove on the upper cartridge, in which an information pattern sticker indicating information related to the plurality of chemicals is positioned; and a point sticker on the upper cartridge, in which the point sticker indicates an insertion direction of the cartridge into the rotating tray.

\* \* \* \* \*